United States Patent
Oren et al.

(10) Patent No.: US 12,336,903 B2
(45) Date of Patent: Jun. 24, 2025

(54) VARIABLE THICKNESS DYNAMIC MEMBRANE FOR ACCOMMODATING INTRAOCULAR LENSES

(71) Applicant: ForSight Vision6, Inc., Brisbane, CA (US)

(72) Inventors: Guy Oren, Brisbane, CA (US); Nicole Kahn-Dror, Brisbane, CA (US); Matthew Clarke, Brisbane, CA (US); Rina Tsvet, Brisbane, CA (US)

(73) Assignee: ForSight Vision6, Inc., South San Francisco, CA (US)

( * ) Notice: Subject to any disclaimer, the term of this patent is extended or adjusted under 35 U.S.C. 154(b) by 0 days.

(21) Appl. No.: 17/575,155

(22) Filed: Jan. 13, 2022

(65) Prior Publication Data
US 2022/0218467 A1    Jul. 14, 2022

Related U.S. Application Data

(60) Provisional application No. 63/136,843, filed on Jan. 13, 2021.

(51) Int. Cl.
*A61F 2/16* (2006.01)

(52) U.S. Cl.
CPC .... *A61F 2/1635* (2013.01); *A61F 2250/0036* (2013.01); *A61F 2250/0053* (2013.01)

(58) Field of Classification Search
CPC .... A61F 2/1635; A61F 2/1613; A61F 2/1624; A61F 2/164; A61F 2002/1681; A61F 2002/1682
See application file for complete search history.

(56) References Cited

U.S. PATENT DOCUMENTS

| | | |
|---|---|---|
| 4,159,546 A | 7/1979 | Shearing |
| 4,373,218 A | 2/1983 | Schachar |
| 4,485,498 A | 12/1984 | Gimbel |
| 4,685,921 A | 8/1987 | Peyman |
| 4,731,078 A | 3/1988 | Stoy et al. |
| 4,734,095 A | 3/1988 | Siepser |
| 4,769,035 A | 9/1988 | Kelman |
| 4,782,820 A | 11/1988 | Woods |
| 4,787,903 A | 11/1988 | Grendahl |
| 4,816,030 A | 3/1989 | Robinson |
| 4,816,031 A | 3/1989 | Pfoff |
| 4,842,601 A | 6/1989 | Smith |

(Continued)

FOREIGN PATENT DOCUMENTS

| | | |
|---|---|---|
| CA | 2944010 A1 | 10/2015 |
| CN | 101137338 A | 3/2008 |

(Continued)

OTHER PUBLICATIONS

U.S. Appl. No. 16/345,364, filed Apr. 26, 2019, US 2019-0269500.

(Continued)

*Primary Examiner* — Christie Bahena
(74) *Attorney, Agent, or Firm* — Mintz Levin Cohn Ferris Glovsky and Popeo, P.C.

(57) ABSTRACT

Intraocular lenses having an anterior optic with a central, dynamic zone configured to undergo shape change for accommodation that has a differential thickness gradient between a posterior surface and an anterior surface. Related devices and methods are provided.

12 Claims, 14 Drawing Sheets

(56) References Cited

U.S. PATENT DOCUMENTS

| | | |
|---|---|---|
| 4,865,601 A | 9/1989 | Caldwell et al. |
| 4,888,012 A | 12/1989 | Horn et al. |
| 4,888,016 A | 12/1989 | Langerman |
| 4,892,543 A | 1/1990 | Turley |
| 4,932,966 A | 6/1990 | Christie et al. |
| 4,932,968 A | 6/1990 | Caldwell et al. |
| 4,957,505 A | 9/1990 | McDonald |
| 5,066,301 A | 11/1991 | Wiley |
| 5,171,266 A | 12/1992 | Wiley et al. |
| 5,171,320 A | 12/1992 | Nishi |
| RE34,424 E | 10/1993 | Walman |
| 5,275,623 A | 1/1994 | Sarfarazi |
| 5,288,293 A | 2/1994 | O'Donnell, Jr. |
| 5,443,506 A | 8/1995 | Garabet |
| 5,489,302 A | 2/1996 | Skottun |
| 5,607,472 A | 3/1997 | Thompson |
| 5,684,637 A | 11/1997 | Floyd |
| 5,766,245 A | 6/1998 | Fedorov et al. |
| 5,774,273 A | 6/1998 | Bornhorst |
| 5,800,806 A | 9/1998 | Yamamoto |
| 5,932,205 A | 8/1999 | Wang et al. |
| 6,013,101 A | 1/2000 | Israel |
| 6,027,531 A | 2/2000 | Tassignon |
| 6,045,535 A | 4/2000 | Ben Nun |
| 6,096,078 A | 8/2000 | McDonald |
| 6,117,171 A | 9/2000 | Skottun |
| 6,120,538 A | 9/2000 | Rizzo, III et al. |
| 6,143,315 A | 11/2000 | Wang et al. |
| 6,188,526 B1 | 2/2001 | Sasaya et al. |
| 6,228,115 B1 | 5/2001 | Hoffmann et al. |
| 6,261,321 B1 | 7/2001 | Kellan |
| 6,277,146 B1 | 8/2001 | Peyman et al. |
| 6,299,641 B1 | 10/2001 | Woods |
| 6,387,126 B1 | 5/2002 | Cumming |
| 6,443,985 B1 | 9/2002 | Woods |
| 6,450,642 B1 | 9/2002 | Jethmalani et al. |
| 6,493,151 B2 | 12/2002 | Schachar |
| 6,506,212 B2 | 1/2003 | Zhou et al. |
| 6,524,340 B2 | 2/2003 | Israel |
| 6,552,860 B1 | 4/2003 | Alden |
| 6,558,420 B2 | 5/2003 | Green |
| 6,592,621 B1 | 7/2003 | Domino |
| 6,599,317 B1 | 7/2003 | Weinschenk, III et al. |
| 6,645,246 B1 | 11/2003 | Weinschenk, III et al. |
| 6,730,123 B1 | 5/2004 | Klopotek |
| 6,733,122 B1 | 5/2004 | Feurer et al. |
| 6,749,634 B2 | 6/2004 | Hanna |
| 6,818,017 B1 | 11/2004 | Shu |
| 6,836,374 B2 | 12/2004 | Esch et al. |
| 6,849,091 B1 | 2/2005 | Cumming |
| 6,851,804 B2 | 2/2005 | Jethmalani et al. |
| 6,855,164 B2 | 2/2005 | Glazier |
| 6,860,601 B2 | 3/2005 | Shadduck |
| 6,930,838 B2 | 8/2005 | Schachar |
| 6,935,743 B2 | 8/2005 | Shadduck |
| 6,966,049 B2 | 11/2005 | Lepejian et al. |
| 6,966,649 B2 | 11/2005 | Shadduck |
| 7,008,449 B2 | 3/2006 | Willis et al. |
| 7,025,783 B2 | 4/2006 | Brady et al. |
| 7,060,094 B2 | 6/2006 | Shahinpoor et al. |
| 7,068,439 B2 | 6/2006 | Esch et al. |
| 7,097,660 B2 | 8/2006 | Portney |
| 7,118,596 B2 | 10/2006 | Zadno-Azizi et al. |
| 7,118,597 B2 | 10/2006 | Miller et al. |
| 7,122,053 B2 | 10/2006 | Esch |
| 7,217,288 B2 | 5/2007 | Esch et al. |
| 7,220,279 B2 | 5/2007 | Nun |
| 7,229,476 B2 | 6/2007 | Azar |
| 7,247,168 B2 | 7/2007 | Esch et al. |
| 7,256,943 B1 | 8/2007 | Kobrin et al. |
| 7,261,737 B2 | 8/2007 | Esch et al. |
| 7,278,739 B2 | 10/2007 | Shadduck |
| 7,293,873 B2 | 11/2007 | Dai et al. |
| 7,341,599 B1 | 3/2008 | Peyman |
| 7,369,321 B1 | 5/2008 | Ren et al. |
| 7,381,221 B2 | 6/2008 | Lang et al. |
| 7,384,429 B2 | 6/2008 | Hanna |
| 7,438,723 B2 | 10/2008 | Esch |
| 7,453,646 B2 | 11/2008 | Lo |
| 7,485,144 B2 | 2/2009 | Esch |
| 7,601,169 B2 | 10/2009 | Phillips |
| 7,615,056 B2 | 11/2009 | Ayton et al. |
| 7,637,947 B2 | 12/2009 | Smith et al. |
| 7,675,686 B2 | 3/2010 | Lo et al. |
| 7,713,299 B2 | 5/2010 | Brady et al. |
| 7,753,953 B1 | 7/2010 | Yee |
| 7,763,069 B2 | 7/2010 | Brady et al. |
| 7,776,088 B2 | 8/2010 | Shadduck |
| 7,806,930 B2 | 10/2010 | Brown |
| 7,854,764 B2 | 12/2010 | Ben Nun |
| 7,857,850 B2 | 12/2010 | Mentak et al. |
| 7,883,540 B2 * | 2/2011 | Niwa .................... A61F 2/1648 |
| | | 623/6.37 |
| 7,976,520 B2 | 7/2011 | Nun |
| 7,985,253 B2 | 7/2011 | Cumming |
| 7,988,285 B2 | 8/2011 | Sandstedt et al. |
| 8,018,658 B2 | 9/2011 | Lo |
| 8,034,106 B2 | 10/2011 | Mentak et al. |
| 8,038,711 B2 | 10/2011 | Clarke |
| 8,158,712 B2 | 4/2012 | Your |
| 8,314,927 B2 | 11/2012 | Choi et al. |
| 8,343,216 B2 | 1/2013 | Brady et al. |
| 8,377,125 B2 | 2/2013 | Kellan |
| 8,414,646 B2 | 4/2013 | De Juan, Jr. et al. |
| 8,500,806 B1 | 8/2013 | Phillips |
| 8,663,235 B2 | 3/2014 | Tassignon |
| 8,668,734 B2 | 3/2014 | Hildebrand et al. |
| 8,715,345 B2 | 5/2014 | DeBoer et al. |
| 8,715,346 B2 | 5/2014 | de Juan, Jr. et al. |
| 8,851,670 B2 | 10/2014 | Dai et al. |
| 8,900,298 B2 | 12/2014 | Anvar et al. |
| 8,956,408 B2 | 2/2015 | Smiley et al. |
| 8,968,396 B2 | 3/2015 | Matthews et al. |
| 8,974,526 B2 | 3/2015 | Bogaert |
| 9,005,282 B2 | 4/2015 | Chang et al. |
| 9,044,317 B2 | 6/2015 | Hildebrand et al. |
| 9,107,748 B2 | 8/2015 | de Juan, Jr. et al. |
| 9,114,005 B2 | 8/2015 | Simonov et al. |
| 9,326,846 B2 | 5/2016 | Devita Gerardi et al. |
| 9,421,089 B2 | 8/2016 | Zadno-Azizi |
| 9,486,311 B2 | 11/2016 | Argento et al. |
| 9,681,981 B2 | 6/2017 | Stevens |
| 9,782,291 B2 | 10/2017 | Stevens |
| 9,814,568 B2 | 11/2017 | Ben Nun |
| 9,872,763 B2 | 1/2018 | Smiley et al. |
| 10,166,096 B2 | 1/2019 | Ben Nun |
| 10,195,018 B2 * | 2/2019 | Salahieh ............... A61F 2/1635 |
| 10,258,805 B2 | 4/2019 | Reed et al. |
| 10,743,983 B2 | 8/2020 | Wortz et al. |
| 10,751,167 B2 | 8/2020 | Paine |
| 11,331,182 B2 * | 5/2022 | de Juan, Jr. ........... A61F 9/0017 |
| 11,337,795 B2 | 5/2022 | Ellis |
| 11,357,618 B2 | 6/2022 | Ellis |
| 2001/0001836 A1 | 5/2001 | Cumming |
| 2002/0188351 A1 | 12/2002 | Laguette |
| 2003/0060878 A1 | 3/2003 | Shadduck |
| 2003/0149480 A1 | 8/2003 | Shadduck |
| 2003/0171809 A1 | 9/2003 | Phillips |
| 2003/0187501 A1 | 10/2003 | Okada |
| 2003/0187504 A1 | 10/2003 | Weinschenk et al. |
| 2004/0006387 A1 | 1/2004 | Kelman |
| 2004/0015140 A1 | 1/2004 | Shields |
| 2004/0034417 A1 | 2/2004 | Heyman |
| 2004/0039446 A1 | 2/2004 | McNicholas |
| 2004/0082993 A1 | 4/2004 | Woods |
| 2004/0082995 A1 | 4/2004 | Woods |
| 2004/0111153 A1 | 6/2004 | Woods et al. |
| 2004/0148023 A1 | 7/2004 | Shu |
| 2004/0162612 A1 | 8/2004 | Portney et al. |
| 2004/0169816 A1 | 9/2004 | Esch |
| 2004/0169820 A1 | 9/2004 | Dai et al. |
| 2004/0237971 A1 | 12/2004 | Radhakrishnan et al. |
| 2005/0021138 A1 | 1/2005 | Woods |
| 2005/0060032 A1 | 3/2005 | Magnante et al. |

(56) References Cited

U.S. PATENT DOCUMENTS

| | | |
|---|---|---|
| 2005/0065534 A1 | 3/2005 | Hohl |
| 2005/0107873 A1* | 5/2005 | Zhou ................. A61F 2/1635 623/6.37 |
| 2005/0113914 A1 | 5/2005 | Miller et al. |
| 2005/0119740 A1* | 6/2005 | Esch ................. A61F 2/1635 623/6.37 |
| 2005/0125059 A1 | 6/2005 | Pinchuk et al. |
| 2005/0137703 A1 | 6/2005 | Chen |
| 2005/0251253 A1 | 11/2005 | Gross |
| 2006/0047340 A1 | 3/2006 | Brown |
| 2006/0064162 A1 | 3/2006 | Klima |
| 2006/0100701 A1 | 5/2006 | Esch et al. |
| 2006/0134173 A1 | 6/2006 | Liu et al. |
| 2006/0238702 A1 | 10/2006 | Glick et al. |
| 2006/0259138 A1 | 11/2006 | Peyman |
| 2007/0010881 A1 | 1/2007 | Soye et al. |
| 2007/0054131 A1 | 3/2007 | Stewart |
| 2007/0078515 A1 | 4/2007 | Brady |
| 2007/0088433 A1 | 4/2007 | Esch et al. |
| 2007/0100444 A1 | 5/2007 | Brady et al. |
| 2007/0123982 A1 | 5/2007 | Yablonski et al. |
| 2007/0129798 A1 | 6/2007 | Chawdhary |
| 2007/0129800 A1 | 6/2007 | Cumming |
| 2007/0129801 A1 | 6/2007 | Cumming |
| 2007/0244561 A1 | 10/2007 | Ben Nun |
| 2008/0046075 A1 | 2/2008 | Esch et al. |
| 2008/0046076 A1 | 2/2008 | Rombach |
| 2008/0097459 A1 | 4/2008 | Kammerlander et al. |
| 2008/0103592 A1 | 5/2008 | Maloney |
| 2008/0106698 A1 | 5/2008 | Dai et al. |
| 2008/0119864 A1 | 5/2008 | Deinzer et al. |
| 2008/0125862 A1 | 5/2008 | Blake |
| 2008/0129962 A1 | 6/2008 | Dai et al. |
| 2008/0288066 A1 | 11/2008 | Cumming |
| 2009/0005865 A1 | 1/2009 | Smiley et al. |
| 2009/0012609 A1 | 1/2009 | Geraghty et al. |
| 2009/0171458 A1 | 7/2009 | Kellan et al. |
| 2009/0204208 A1* | 8/2009 | Simpson ............... A61F 2/1613 623/6.23 |
| 2009/0234449 A1 | 9/2009 | De Juan, Jr. et al. |
| 2009/0292355 A1 | 11/2009 | Boyd et al. |
| 2010/0094415 A1 | 4/2010 | Bumbalough |
| 2010/0121444 A1 | 5/2010 | Ben Nun |
| 2010/0280609 A1 | 11/2010 | Simonov et al. |
| 2011/0054600 A1 | 3/2011 | Bumbalough |
| 2011/0071628 A1 | 3/2011 | Gross et al. |
| 2011/0112636 A1 | 5/2011 | Ben Nun |
| 2011/0118834 A1 | 5/2011 | Lo et al. |
| 2012/0078364 A1 | 3/2012 | Stenger |
| 2012/0168422 A1 | 7/2012 | Boyd et al. |
| 2012/0253459 A1* | 10/2012 | Reich ................. A61F 2/1624 623/6.46 |
| 2013/0013061 A1 | 1/2013 | Coroneo |
| 2013/0041382 A1 | 2/2013 | Ben Nun |
| 2013/0110235 A1 | 5/2013 | Schwiegerling |
| 2013/0116781 A1 | 5/2013 | Ben Nun |
| 2013/0245754 A1 | 9/2013 | Blum et al. |
| 2014/0012240 A1 | 1/2014 | Ho et al. |
| 2014/0058507 A1 | 2/2014 | Reich et al. |
| 2014/0074074 A1 | 3/2014 | Dick et al. |
| 2014/0121768 A1 | 5/2014 | Simpson |
| 2014/0180403 A1 | 6/2014 | Silvestrini et al. |
| 2014/0228949 A1 | 8/2014 | Argento et al. |
| 2014/0277437 A1* | 9/2014 | Currie ................. A61F 2/1624 623/6.37 |
| 2015/0150676 A1 | 6/2015 | Nun |
| 2015/0250584 A1 | 9/2015 | Blum et al. |
| 2015/0257874 A1 | 9/2015 | Hildebrand et al. |
| 2016/0008126 A1 | 1/2016 | Salahieh et al. |
| 2016/0030161 A1* | 2/2016 | Brady ................. A61F 2/1629 623/6.13 |
| 2017/0342096 A1 | 11/2017 | Silvestrini |
| 2018/0177589 A1 | 6/2018 | Argento et al. |
| 2019/0038401 A1 | 2/2019 | Reich et al. |
| 2019/0183637 A1 | 6/2019 | Ben Nun |
| 2019/0223998 A1* | 7/2019 | de Juan, Jr. ........... A61F 2/1635 |
| 2019/0223999 A1 | 7/2019 | Nun |
| 2019/0269500 A1 | 9/2019 | de Juan, Jr. et al. |
| 2020/0179104 A1 | 6/2020 | Brady et al. |
| 2020/0188088 A1 | 6/2020 | Reich et al. |
| 2021/0378815 A9 | 12/2021 | Salahieh et al. |
| 2024/0050222 A1 | 2/2024 | Salahieh et al. |

FOREIGN PATENT DOCUMENTS

| | | |
|---|---|---|
| CN | 101795642 A | 8/2010 |
| CN | 103025271 A | 4/2013 |
| CN | 103096837 A | 5/2013 |
| CN | 105392448 A | 3/2016 |
| EP | 0 162 573 A2 | 11/1985 |
| EP | 1 917 932 A1 | 5/2008 |
| EP | 1 932 492 B1 | 9/2011 |
| EP | 2535019 A1 * | 12/2012 ........... A61F 2/1602 |
| JP | 2005169131 A | 6/2005 |
| JP | 2005533611 A | 11/2005 |
| JP | 2008-532617 A | 8/2008 |
| JP | 2008183434 A | 8/2008 |
| JP | 2009532176 A | 9/2009 |
| JP | 2011500270 A | 1/2011 |
| JP | 2016525432 A | 8/2016 |
| WO | WO-93/03686 A2 | 3/1993 |
| WO | WO-03/000154 A2 | 1/2003 |
| WO | WO-03/017867 A2 | 3/2003 |
| WO | WO-03/017873 A1 | 3/2003 |
| WO | WO-2004/010905 A2 | 2/2004 |
| WO | WO-2004/037122 A2 | 5/2004 |
| WO | WO-2004/037127 A2 | 5/2004 |
| WO | WO-2004/053568 A1 | 6/2004 |
| WO | WO-2004/107024 A1 | 12/2004 |
| WO | WO-2005/057272 A2 | 6/2005 |
| WO | WO-2005/082285 A1 | 9/2005 |
| WO | WO-2007/113832 A2 | 10/2007 |
| WO | WO-2007/117476 A2 | 10/2007 |
| WO | WO-2008/031231 A1 | 3/2008 |
| WO | WO-2009/055099 A1 | 4/2009 |
| WO | WO-2010/010565 A2 | 1/2010 |
| WO | WO-2012/006186 A2 | 1/2012 |
| WO | WO-2012/023133 A1 | 2/2012 |
| WO | WO-2012/067994 A2 | 5/2012 |
| WO | WO-2013/016804 A1 | 2/2013 |
| WO | WO-2015/066502 A1 | 5/2015 |
| WO | WO-2015/148673 A1 | 10/2015 |
| WO | WO-2016/140708 A1 | 9/2016 |
| WO | WO-2016201351 A1 * | 12/2016 ............... A61F 2/16 |
| WO | WO-2017/087358 A1 | 5/2017 |
| WO | WO-2017/096087 A1 | 6/2017 |
| WO | WO-2018/081595 A1 | 5/2018 |
| WO | WO-2018/222579 A1 | 12/2018 |
| WO | WO-2018/227014 A1 | 12/2018 |
| WO | WO-2018/081595 A8 | 6/2019 |
| WO | WO-2020/206343 A1 | 10/2020 |
| WO | WO-2021/257518 A1 | 12/2021 |

OTHER PUBLICATIONS

U.S. Appl. No. 16/372,090, filed Apr. 1, 2019, US 2019-0223998.

PCT/US21/37354, Jun. 15, 2021, WO 2021/257518.

Choi, S. T. (2014). "Opto-mechanical analysis of nonlinear elastomer membrane deformation under hydraulic pressure for variable-focus liquid-filled microlenses." Optics Express, 22(5): 6133-6146. https://doi.org/10.1364/OE.22.006133.

Gimbel, H.V., Debroff, B.M. (2004), "Intraocular lens optic capture." J Cataract Refract Surg Jan. 2004;30 (1):200-6.

Shaw, D. et al. (2007). "Optical properties of variable-focus liquid-filled optical lenses with different membrane shapes." Optical Engineering. 46(2):024002-1_024002-6. Web. Sep. 7, 2012.

Zhao, P. (2015). "Spherical aberration free liquid-filled tunable lens with variable thickness membrane." Optics Express. 23(6): 21264-21278. 10.1364/OE.23.021264.

U.S. Appl. No. 17/364,202, filed Jun. 30, 2021, US 2022-0160495.

PCT/US2022/47293, Oct. 20, 2022, WO 2023/069630.

(56) References Cited

OTHER PUBLICATIONS

U.S. Appl. No. 17/166,680, filed Feb. 3, 2021, US 2021-0259826.
U.S. Appl. No. 17/221,525, filed Apr. 2, 2021, US 2021-0290372.
U.S. Appl. No. 17/722,154, filed Apr. 15, 2022, US 2022-0323205.
PCT/US2023/60967, Jan. 20, 2023, WO 2023/141552.
PCT/US2023/16450, Mar. 27, 2023, WO 2023/192202.
U.S. Appl. No. 17/600,571, filed Sep. 30, 2021, US 2022-0168464.
U.S. Appl. No. 17/970,131, filed Oct. 20, 2022, US 2023-0129111.
U.S. Appl. No. 17/979,675, filed Nov. 2, 2022, US 2023-0240835.
U.S. Appl. No. 18/010,616, filed Dec. 15, 2022, US 2023-0383062.
U.S. Appl. No. 18/593,830, filed Mar. 1, 2024, US 2024-0315832.
PCT/US2023/31047, Aug. 24, 2023, WO 2024/044312.
PCT/US2023/36284, Oct. 30, 2023, WO 2024/097132.

\* cited by examiner

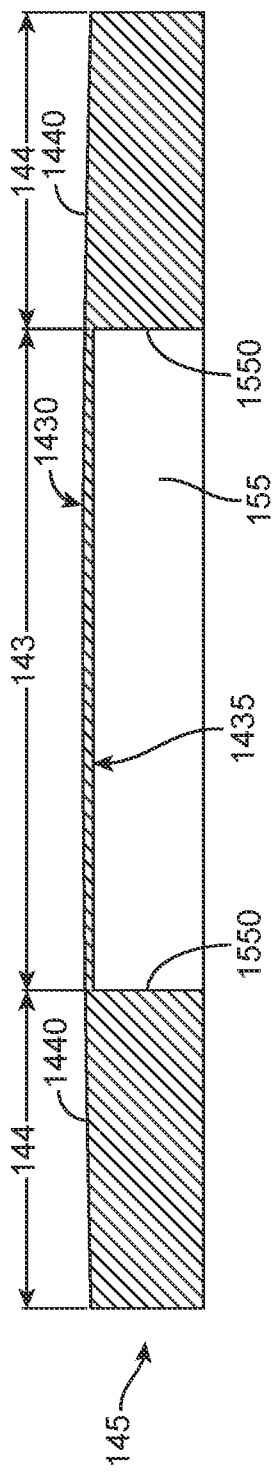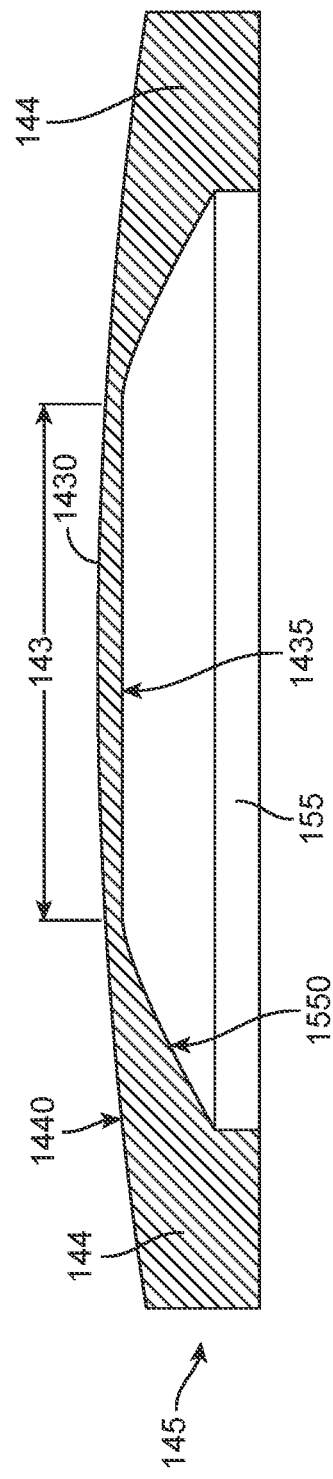

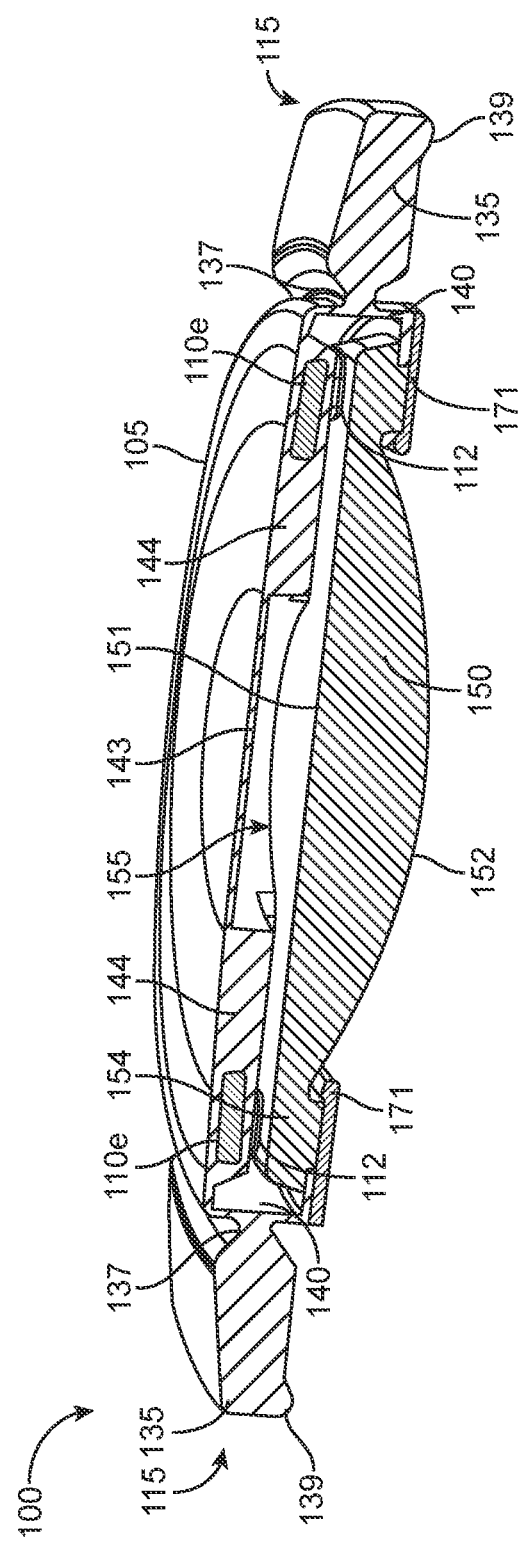

VARIABLE THICKNESS DYNAMIC MEMBRANE FOR ACCOMMODATING INTRAOCULAR LENSES

CROSS-REFERENCE TO PRIORITY DOCUMENT

The present application claims the benefit of priority to U.S. Provisional Application Ser. No. 63/136,843, filed Jan. 13, 2021. The full disclosure is incorporated herein by reference in its entirety.

BACKGROUND

A healthy, young human eye can focus an object in far or near distance, as required. The capability of the eye to change back and forth from near vision to far vision is called accommodation. Accommodation occurs when the ciliary muscle contracts to thereby release the resting zonular tension on the equatorial region of the capsular bag. The release of zonular tension allows the inherent elasticity of the lens to alter to a more globular or spherical shape, with increased surface curvatures of both the anterior and posterior lenticular surfaces.

The human eye 10 includes a cornea 12, iris 14, sulcus 16, ciliary muscle 18, zonules 20, a lens 21 contained within a capsular bag 22 (FIGS. 1A and 1C). Accommodation occurs when the ciliary muscle 18 contracts to thereby release the resting zonular tension on the equatorial region of the capsular bag 22. The release of zonular tension allows the inherent elasticity of the lens 21 to alter to a more globular or spherical shape, with increased surface curvatures of both the anterior lenticular surface 23 and posterior lenticular surface 24. In addition, the human lens can be afflicted with one or more disorders that degrade its functioning in the vision system. A common lens disorder is a cataract which is the opacification of the normally clear, natural crystalline lens matrix 26. The opacification can result from the aging process but can also be caused by heredity, diabetes, or trauma. FIG. 1A shows a lens capsule comprising a capsular bag 22 with an opacified, crystalline lens nucleus 26.

In a cataract procedure, the patient's opaque crystalline lens is replaced with a clear lens implant or intraocular lens (IOL) 30. In conventional extracapsular cataract surgery as depicted in FIG. 1B, the crystalline lens matrix 26 is removed leaving intact the thin walls of the anterior and posterior capsules together with zonular ligament connections to the ciliary body and ciliary muscles 18. The crystalline lens core is removed by phacoemulsification through a curvilinear capsulorhexis as illustrated in FIG. 1B, i.e., the removal of an anterior portion 23 of the capsular sac. FIG. 1B depicts a conventional 3-piece IOL 30 just after implantation in the capsular bag 22.

It is known to implant a combination of lenses to address refraction errors in the existing lens in the case of phakic IOLs or improve the refractive results of standard IOL after cataract surgery in the case of pseudophakic patients. These "piggyback" IOLs can be placed anterior to the previously implanted IOL or natural lens to improve the refractive results of cataract surgery in the case of pseudophakes or to change the refractive status of the eye in the case of phakic eyes, usually to correct high myopia. Generally, these lenses are implanted in the ciliary sulcus and are non-accommodating. As shown in FIG. 1C, the ciliary sulcus 16 is the space between the posterior surface of the base of the iris 14 and the anterior surface of the ciliary body. FIG. 1C also shows the angle of the anterior chamber 25 of the eye.

IOLs are typically implanted after cataract extractions. Generally, IOLs are made of a foldable material, such as silicone or acrylics, for minimizing the incision size and improving patient recovery time. Most commonly used IOLs are single-element lenses that provide a single focal distance for distance vision. Accommodating intraocular lenses (AIOLs) have also been developed to provide adjustable focal distances (or accommodations) that rely on the natural focusing ability of the eye, for example, as described in US 2009/0234449, US 2009/0292355, US 2012/0253459, U.S. Pat. No. 10,258,805, and US 2019/0269500, which are each incorporated by reference herein in their entireties. AIOLs are beneficial for patients not suffering from cataracts, but who wish to reduce their dependency on glasses and contacts to correct their myopia, hyperopia and presbyopia. Intraocular lenses used to correct large errors in myopic, hyperopic, and astigmatic eye are called "phakic intraocular lenses" and are implanted without removing the crystalline lens. In some cases, aphakic IOLs (not phakic IOLs) are implanted via lens extraction and replacement surgery even if no cataract exists. During this surgery, the crystalline lens is extracted and an IOL replaces it in a process that is very similar to cataract surgery. Refractive lens exchange, like cataract surgery, involves lens replacement, requires making a small incision in the eye for lens insertion, use of local anesthesia and lasts approximately 30 minutes.

IOLs, particularly accommodating IOLs, may incorporate liquids in fluid chambers such that accommodation is achieved with the help of fluid-actuated mechanisms. A force exerted on a portion of the lens is transmitted via the fluid to deform a flexible layer of the lens resulting in accommodative shape change of the IOL. For example, ciliary muscle movements of the eye may be harnessed by components of an AIOL to drive shape change and accommodation. The AIOLs can achieve an optical power or diopter (D) in a desired range due to shape change of the optic upon application of a small amount of force (e.g., as little as 0.1-1.0 grams force (gf)) applied by the eye tissue. The AIOLs provide reliable dioptric change by harnessing small forces. A chamber for containing liquid materials that is formed by flexible layers of elastomeric material can change shape and thus, power of the lens depending on the volume of liquid. As fill volume increases beyond the chamber volume, the flexible layers can bulge outward creating a lens with a greater focal length.

There is need in the art for improved flexible layers of the shape changing lens that provide improved properties for patients in need. The disclosure is directed to this, as well as other, important ends.

SUMMARY

Provided is an accommodating intraocular lens having an anterior optic. The anterior optic includes a central, dynamic zone configured to undergo shape change for accommodation having a dynamic membrane with a differential thickness gradient between a posterior surface and an anterior surface of the dynamic membrane. The anterior optic includes a peripheral static zone having a static anterior optical portion configured to resist shape change. The optic also includes a non-compressible optical fluid contained within a fluid chamber defined, in part, by the posterior surface of the dynamic membrane. Compression of the fluid chamber at a first region causes the shape change of the central, dynamic zone for accommodation.

The anterior surface of the dynamic membrane can be convex and the posterior surface of the dynamic membrane can be plano. The anterior surface can control the differential thickness gradient of the dynamic membrane and the gradient can change gradually between a periphery and a center of the dynamic membrane. The anterior surface of the dynamic membrane can have a convex curvature that is single radius or aspheric equation. The static anterior optical portion can have an anterior surface that has a curvature that is the same or different from the convex curvature of the anterior surface of the dynamic membrane. The anterior surface of the dynamic membrane can be convex and the posterior surface of the dynamic membrane can be convex. Both the anterior surface and the posterior surface can control the differential thickness gradient of the dynamic membrane and the gradient can change rapidly between a periphery and a center of the dynamic membrane. The anterior surface of the dynamic membrane can have a convex curvature that is single radius or aspheric equation. The posterior surface of the dynamic membrane can have a convex curvature that is single radius or aspheric equation. The static anterior optical portion can have an anterior surface that has a curvature that is the same or different from the convex curvature of the anterior surface of the dynamic membrane. The anterior surface of the dynamic membrane can be convex and the posterior surface of the dynamic membrane can be concave. Both the anterior surface and the posterior surface can control the differential thickness gradient of the dynamic membrane and the gradient change gradually between a periphery and a center of the dynamic membrane. The anterior surface of the dynamic membrane can have a convex curvature that is single radius or aspheric equation. The posterior surface of the dynamic membrane can have a concave curvature that is single radius or aspheric equation. The static anterior optical portion can have an anterior surface that has a curvature that is the same or different from the convex curvature of the anterior surface of the dynamic membrane.

The anterior surface of the dynamic membrane can be convex and the posterior surface of the dynamic membrane can be convex at a periphery of the dynamic membrane and plano near a center of the dynamic membrane. Both the anterior surface and the posterior surface can control the differential thickness gradient of the dynamic membrane near the periphery and only the anterior surface controls the differential thickness gradient of the dynamic membrane at the center. The gradient can change non-linearly between the periphery and the center of the dynamic membrane. The anterior surface of the dynamic membrane can have a convex curvature that is single radius or aspheric equation. The posterior surface of the dynamic membrane near the periphery can have a concave curvature that is single radius or aspheric equation. The static anterior optical portion can have an anterior surface that has a curvature that is the same or different from the convex curvature of the anterior surface of the dynamic membrane near the periphery. The anterior surface of the dynamic membrane after accommodation can be spherical and the optical fluid can have a refractive index that is higher than or equal to a refractive index of the anterior optic. The anterior surface of the dynamic membrane after accommodation can be aspherical, and the optical fluid have a refractive index that is lower than a refractive index of the anterior optic.

BRIEF DESCRIPTION OF THE DRAWINGS

These and other aspects will now be described in detail with reference to the following drawings. Generally, the figures are exemplary and are not to scale in absolute terms or comparatively but are intended to be illustrative. Relative placement of features and elements is modified for the purpose of illustrative clarity.

FIG. 2B is a cross-sectional view of an accommodating intraocular lens taken along line B-B of FIG. 2A;

FIGS. 3A-3D are cross-sectional views of the lens of FIG. 2B illustrating different anterior optic geometries;

FIG. 3I-1 is an image of an anterior membrane using optical metrology equipment to assess optical quality of the lens having solid and liquid components where the liquid component has an RI that is lower than that of the solid component;

FIG. 3I-2 is a schematic of FIG. 3I-1 illustrating the light beams passing through the solid and liquid components of the lens;

FIG. 3J-1 is an image of an anterior membrane using optical metrology equipment to assess optical quality of the lens having solid and liquid components where the liquid component has an RI that is index-matched to that of the solid component;

FIG. 3J-2 is a schematic of FIG. 3J-1 illustrating the light beams passing through the solid and liquid components of the lens;

FIGS. 4E and 4F are cross-sectional views of the lens of FIG. 4A;

DETAILED DESCRIPTION

It is important to have quality optics in lenses, particularly intraocular lenses (IOL), that avoid stray light, glare, or unintended reflections that reach the retina. Generally, lenses allow light that is refracted by the optically designed lens surfaces to reach the retina. Light from the edge of a lens at the non-optical interface between the lens edge and the aqueous humor can cause dysphotopsias common in commercial lenses known in the art known. Dysphotopsias can be an annoyance to patients. Similarly, any interface between two materials of varying refractive index within the lens may cause light to reach a patient's retina in a way that disturbs clear, quality vision. Maintaining a predictable shape of the lens throughout its useful life, particularly during and after shape change of the lens, provides the correct optical power to properly focus light onto a patient's retina.

The lenses described herein harnesses movements of ciliary tissue to deform a wall of the lens body also referred to herein as a dynamic optical membrane into an expanded shape for near vision. Described herein are lens bodies having wall portions or optical membranes having controlled continuous thickness gradient between the periphery to the center that under application of a uniform pressure load on the optical fluid chamber deflects to a desired optical surface shape for near vision.

Figure 1A:
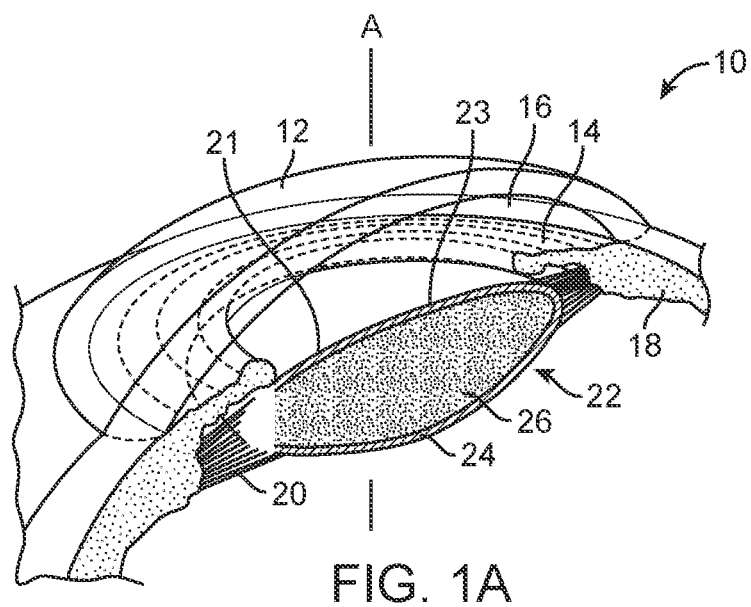
FIG. 1A is a perspective cut-away view of an eye with an opacified lens capsule.
Figure 1B:
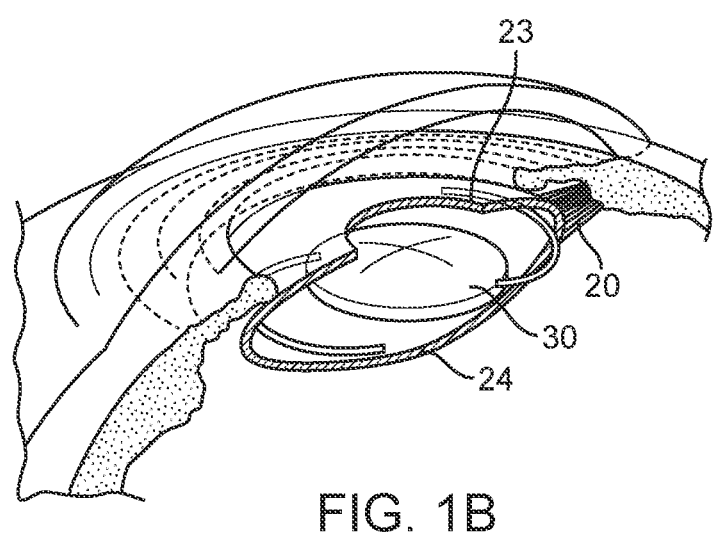
FIG. 1B is a perspective cut-away view of the eye of FIG. 1A with a curvilinear capsulorhexis and the crystalline lens matrix removed with the implantation of a traditional 3-piece IOL.
Figure 1C:
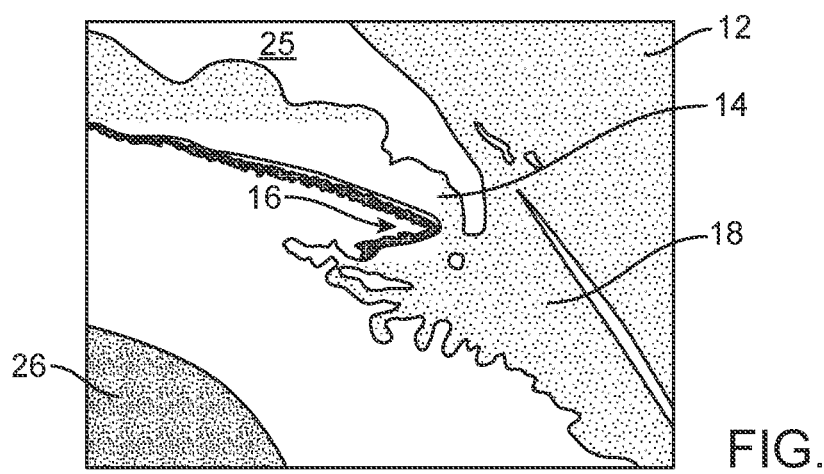
FIG. 1C is a cross-sectional view of an anterior angle of an eye.
Figure 2A:
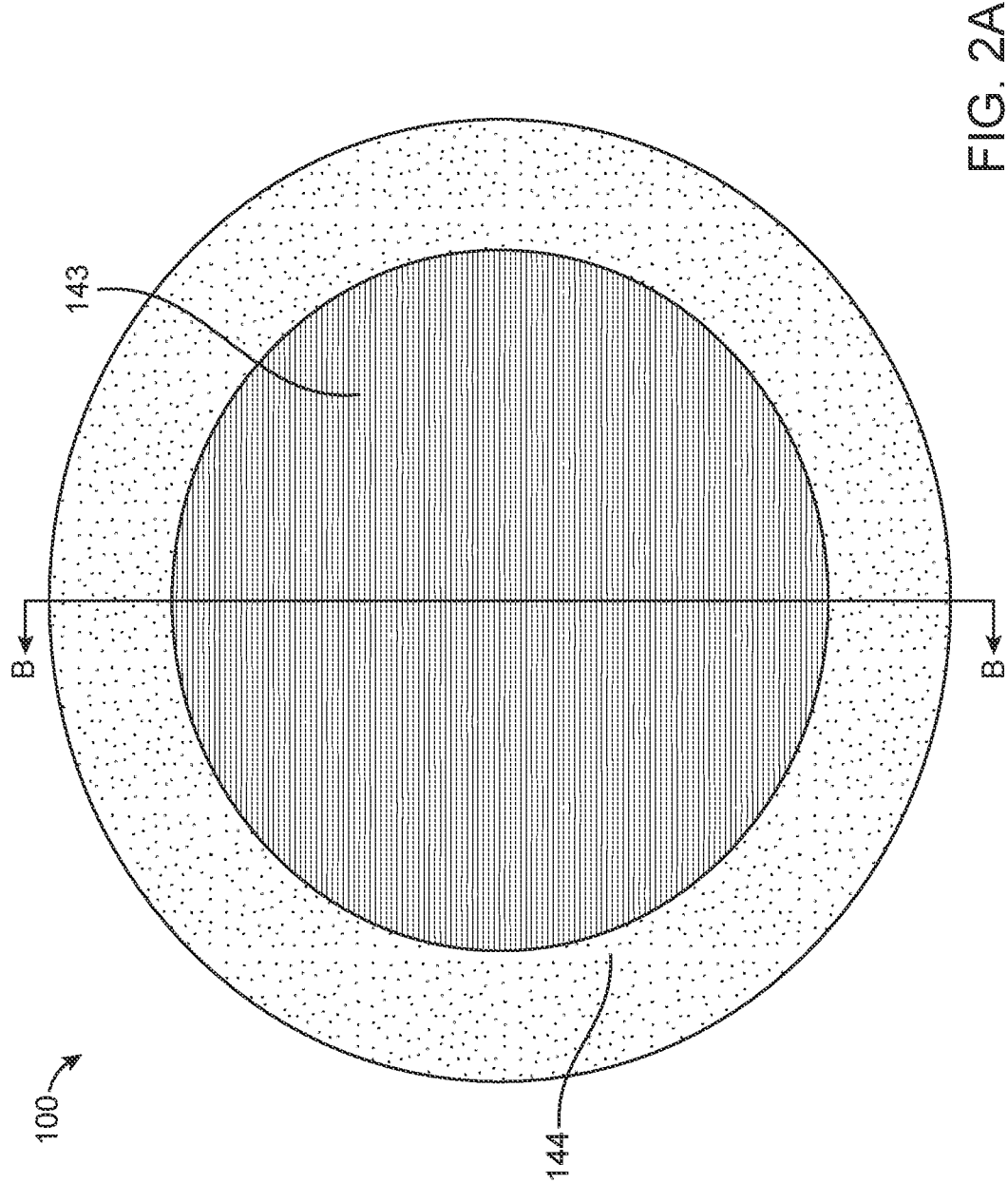
FIG. 2A is a top down view of an accommodating intraocular lens in schematic.

FIGS. 2A-2B illustrate in schematic partial views of an accommodating intraocular lens that generally includes solid optical component and liquid optical material. The lens 100 can include an anterior optic 145 having a central, dynamic zone formed by a dynamic membrane 143 that is surrounded by a peripheral, static zone formed by a static anterior optical portion 144. The dynamic membrane 143 of the anterior optic 145 is configured to undergo shape change for accommodation whereas the static anterior optical portion 144 of the anterior optic 145 is configured to resist shape change. The dynamic membrane 143 can have a differential thickness gradient to provide precise control over the shape of the membrane 143 and overall optical performance during shape change. The dynamic membrane 143 can be designed to have different thickness gradients to provide a different membrane shape that provides the best optical performance for a particular AIOL. The thickness gradient across the dynamic membrane 143 can be defined by the curvatures of the anterior (external) surface 1430 and the posterior (internal) surface 1435 of the dynamic membrane 143, and in some implementations the curvature of the anterior surface 1440 of the static anterior optical portion 144 (see FIG. 3A). The specific curvature combinations of the anterior surfaces 1430, 1440 and posterior surface 1435 of the dynamic membrane 143 can provide improved optical quality.

The terms "anterior" and "posterior" as used herein are used to denote a relative frame of reference, position, direction or orientation for understanding and clarity. Use of the terms is not intended to be limiting to the structure and/or implantation of the lens. For example, the orientation of the lens within the eye can vary such that the anterior optic 145 can be positioned anteriorly along the optical axis A of the lens 100 relative to the eye anatomy and the anterior surface faces towards the cornea and the posterior surface faces towards the retina. However, the anterior optic 145 can be positioned posteriorly relative to the eye anatomy. A membrane as used herein may denote a wall portion of the lens body that forms part of the sealed fluid chamber of the lens body that contains the non-compressible optical fluid that is generally configured to move upon application of a force during use of the IOL to achieve accommodative shape change of the lens body.

Still with respect to FIG. 2B, the solid optical component of the lens 100 creates a sealed, fixed volume fluid chamber 155 that contains a fixed volume of the liquid optical material. The fluid chamber 155 can be defined, in part, by internal sidewalls 1550 that can be vertical, sloped, curved, or a combination thereof. The geometry of the sidewalls 1550 of the chamber 155 and thus, the geometry of the dynamic membrane 143 and static anterior optical portion 144 can vary. The geometry selected for the solid component can depend on whether the liquid optical material to be contained within the chamber 155 of the lens will have the same refractive index as the solid optical component or a different refractive index, which will be described in more detail below.

The anterior optic 145 can have an external, anterior-facing surface that is convex with a single radius of curvature or different radii. The anterior radius of curvature can be defined as the distance between a central, fixed point within the lens body and the anterior surface 1430 of the dynamic membrane 143. A constant, single radius profile is one that follows a regular arc where the anterior surface 1430 of the membrane 143 is always the same distance from the central point. An aspheric profile deviates from the regular spherical curve so that no single radius of curvature can be used to define their overall shape. For example, the anterior surface 1440 of the static anterior optical portion 144 can have an anterior radius of curvature and the anterior surface 1430 of the dynamic membrane 143 can have a different anterior radius of curvature. The anterior radius of curvature of the dynamic membrane 143 can be greater than, less than, or equal to the anterior radius of curvature of the static anterior optical portion 144. The posterior surface 1435 of the anterior optic 145 can be convex, concave, plano, or a combination of convex/plano or concave/plano. As with the anterior surfaces, the posterior surface 1435 can have a posterior radius of curvature that is a single radius of curvature or different radii, spherical or aspheric equation. The change of curvature of the anterior surfaces, the posterior surface, or a combination of the anterior and posterior surfaces can control the differential thickness gradient over the dynamic membrane 143 and/or the static anterior optical portion 144.

Generally, the dynamic membrane 143 of the central, dynamic zone of the anterior optic 145 is substantially thinner than the static anterior optical portion 144 at the periphery of the anterior optic (see FIGS. 2B and 3A-3D). Due to the curvatures of one or both of the anterior surface 1430 and posterior surface 1435, the dynamic membrane 143 can have a controlled continuous thickness gradient between the periphery of the membrane near the static anterior optical portion 144 and the center.

FIG. 3A is a schematic illustration of one implementation of an anterior optic 145 showing the anterior surface 1430 of the dynamic membrane 143 and the anterior surface 1440 of the static anterior optical portion 144 as well as the posterior surface 1435 of the dynamic membrane 143. The anterior surfaces 1430, 1440 are convex and can have the same curvature or different curvatures. For example, the anterior surfaces can have a spherical, single radius profile or an aspheric profile. The posterior surface 1435 of the dynamic membrane 143 can be plano. The surface controlling the differential thickness gradient in this implementation is the anterior surface 1430 of the dynamic membrane 143, which creates a gradual change in thickness from the peripheral regions of the lens towards the center.

The aspheric surface profiles can be designed using the aspheric equation:

$$z(r) = \frac{r^2}{R\left(1 + \sqrt{1-(1+\kappa)\frac{r^2}{R^2}}\right)} + \alpha_4 r^4 + \alpha_6 r^6 + \cdots,$$

where the optic axis is presumed to lie in the z direction, and Z(r) is the sag—the z-component of the displacement of the surface from the vertex, at distance r from the axis. The coefficients $\alpha_i$ describe the deviation of the surface from the axially symmetric quadric surface specified by r and κ. If the coefficients $\alpha_i$ are all zero, then R is the radius of curvature and κ is the conic constant, as measured at the vertex (where r=0). In this case, the surface has the form of a conic section rotated about the optic axis, with form determined by κ according to Table 1 below.

TABLE 1

| | Conic Section |
|---|---|
| κ < −1 | Hyperbola |
| κ = −1 | Parabola |
| −1 < κ < 0 | Ellipse (surface is a prolate spheroid) |
| κ = 0 | Sphere |
| κ > 0 | Ellipse (surface is an oblate spheroid) |

Figure 3B:
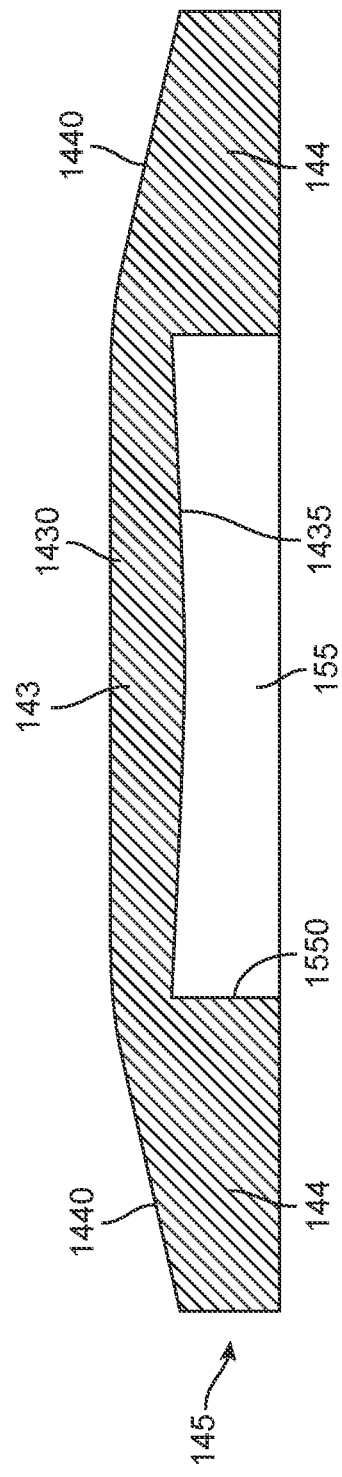

FIG. 3B is a schematic illustration of an anterior optic 145 showing a different differential thickness gradient. The anterior surfaces 1430, 1440 are convex and can have the same curvature or different curvatures. The posterior surface 1435 of the dynamic membrane 143 can also be convex curvature, which can be single radius or aspheric equation. Both the anterior and posterior surfaces control the differential thickness gradient in this implementation creating a rapid change in thickness from the peripheral regions of the lens towards the center.

Figure 3C:
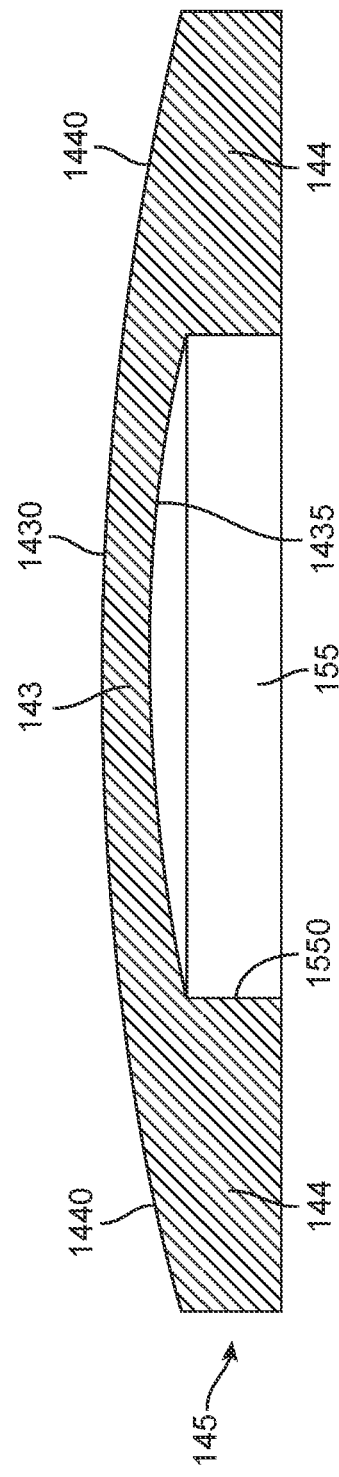

FIG. 3C is a schematic illustration of an anterior optic 145 showing another differential thickness gradient. The anterior surfaces 1430, 1440 are convex and can have the same curvature or different curvatures and the curvatures can be single radius or aspheric equation curvatures. The posterior surface 1435 of the dynamic membrane 143 can be concave curvature, which can be single radius or aspheric equation. Both the anterior and posterior surfaces control the differential thickness gradient in this implementation, but create a gradual change in thickness from the peripheral regions of the lens towards the center.

Figure 3D:
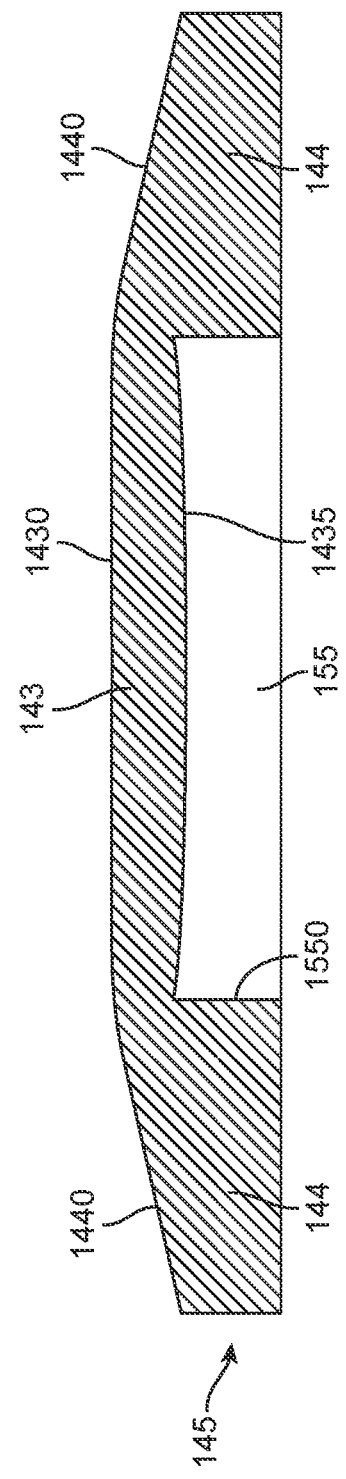

FIG. 3D is a schematic illustration of an anterior optic 145 showing another differential thickness gradient. The anterior surfaces 1430, 1440 are convex and can have the same curvature or different curvatures and the curvatures can be single radius or aspheric equation curvatures. The posterior surface 1435 of the dynamic membrane 143 can be convex at the periphery and plano in the center. Both the anterior and posterior surfaces at the periphery control the differential thickness gradient and the anterior surface controls the gradient only at the center. This implementation creates a non-linear thickness gradient.

The cross-sectional thickness of the dynamic membrane 143 can be the greatest at the center. The thickness at the center can be between 5-30 microns thicker than the thickness of the dynamic membrane 143 at the periphery near the static anterior optical portion 144. The center of the dynamic membrane 143 can be greater than 50 microns up to about 70 microns, or up to about 80 microns, or up to about 90 microns, or up to about 100 microns, or up to about 200 microns and anywhere in between these ranges. In an implementation, the periphery of the dynamic membrane 143 can have a cross-sectional thickness that is about 50 microns to about 70 microns and the center of the dynamic membrane 143 can have a cross-sectional thickness that is about 60 microns to about 80 microns.

The cross-sectional thickness of the static anterior optical portion 144 can also vary between its outer-most perimeter and more central region. FIG. 2B shows the cross-sectional thickness of the static anterior optical portion 144 is substantially uniform between the peripheral region and the central region near where it borders the dynamic membrane 143. The static anterior optical portion 144 can have anterior radius of curvature resulting in a slightly thinner periphery compared to the central region. FIG. 3A shows the cross-sectional thickness of the static anterior optical portion 144 can change between the peripheral region and the central region near the dynamic membrane 143 beyond that due to the anterior radius of curvature. The inner-facing sidewalls 1550 formed by the static anterior optical portion 144 can taper in cross-sectional thickness centrally towards the dynamic membrane 143. As an example, the outer-most peripheral region of the static anterior optical portion 144 can have a first cross-sectional thickness. This peripheral region of the static anterior optical portion 144 can have substantially vertical internal sidewalls 1550 defining the chamber 155. The central region of the static anterior optical portion 144 can having internal sidewalls 1550 that slope away from vertical toward the dynamic membrane 143. The cross-sectional thickness of the static anterior optical portion 144 decreases centrally approaching the cross-sectional thickness of the dynamic membrane 143.

The diameter of the dynamic membrane 143 can vary and can be different depending on the geometry of the sidewalls 1550 forming the chamber 155. As discussed above and as shown in FIG. 2B, the internal sidewalls 1550 formed by the static anterior optical portion 144 can be substantially vertical (posterior-to-anterior) such that the angle between the sidewall 1550 and the inner surface of the dynamic membrane 143 is about 90 degrees. The diameter of the dynamic membrane 143 can be the substantially same as the diameter of the chamber 155, for example, about 2.5 mm to about 3.1 mm, or about 2.0 mm to about 4.0 mm. In another implementation, the internal sidewalls 1550 formed by the static anterior optical portion 144 can be substantially vertical in a first, more peripheral region creating a first portion of the chamber 155 having a height of about 50-500 microns and the internal sidewalls 1550 formed by the static anterior optical portion 144 can be sloping or angled in a second, more central region creating a second portion of the chamber 155 having a height of about 100-600 microns (see FIG. 3A). The angle between the sidewall 1550 and the inner surface of the dynamic membrane 143 in this implementation can be greater than 90 degrees, such as about 130 degrees to about 170 degrees. The sloping internal surface of the static anterior optical portion 144 can result in the diameter of the dynamic membrane 143 to be less than the diameter of the first portion of the chamber 155 where the walls of the static anterior optical portion 144 are vertical. For example, the dynamic membrane diameter can be about 1.7 mm to about 3.0 mm compared to the diameter of the first portion of the chamber 155, which can be about 3.5 mm to about 5.0 mm.

The static anterior optical portion 144 can be between about 300 microns and 700 microns thick anterior-to-posterior at its outermost periphery. The dynamic membrane 143, in contrast, can be thinner. In some implementations, the dynamic membrane 143 can be no greater than about 80 microns at its thickest point, or no greater than about 90 microns, or no greater than about 100 microns, or no greater than 150 microns, or no greater than about 200 microns at its thickest point and anywhere in between these ranges. In some implementations, the center of the dynamic membrane 143 has a greater thickness than the periphery of the dynamic membrane. For example, the center of the dynamic membrane 143 can be greater than 60 microns up to about 80 microns, or up to about 90 microns, or up to about 100 microns, or up to about 200 microns and anywhere in between these ranges. The periphery of the dynamic membrane can be less than the center, for example, by 10 to about 30 microns thinner. In other implementations, the periphery of the dynamic membrane 143 has a greater thickness than the center. In still further implementations, the center and the periphery are thicker than a region of the membrane 143 between them.

Figure 3E:
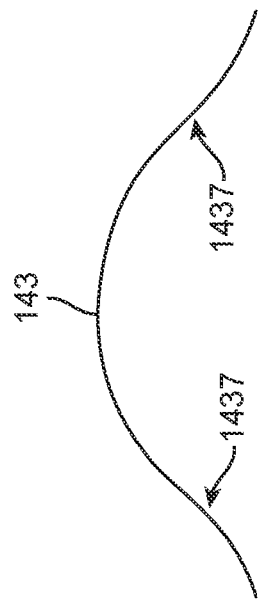
FIG. 3E is a cross-sectional view of a lens illustrating anterior optic geometry.
Figure 3F:
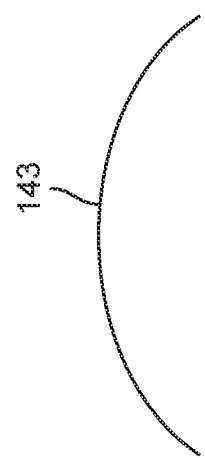
FIG. 3F is a schematic view of a dynamic membrane of the lens of FIG. 3E having an accommodated shape that is aspheric.

The geometry of the chamber 155, the dynamic membrane 143, and the static anterior optical portion 144 can be designed in combination with the refractive index (RI) of the solid component (e.g., silicone elastomer) and liquid component (e.g., silicone oil) of the lens. An external shape of the dynamic membrane 143 upon shape change may be aspheric and does not have a single radius of curvature (see FIGS. 3E-3F). Rather, the local radius of curvature varies between the center of the membrane 143 and the peripheral edge of the membrane 143. The change in curvature over the surface can create a transition zone 1437 where the curvature changes from convex to concave (see FIG. 3F). The concave part of the curve can create optical aberrations that become more severe the higher the refractive index of the liquid component within the chamber. The aberrations can be controlled by adjusting the RI of the components, but some aberrations become too severe to be corrected. Thus, membrane designs that are aspheric and incorporate transition zones in the curvature upon shape change are preferred with liquid component that has an RI lower than the RI of the solid component. In such cases where a transition zone is incorporated, it is advantageous to limit the width of the transition zone.

Figure 3G:
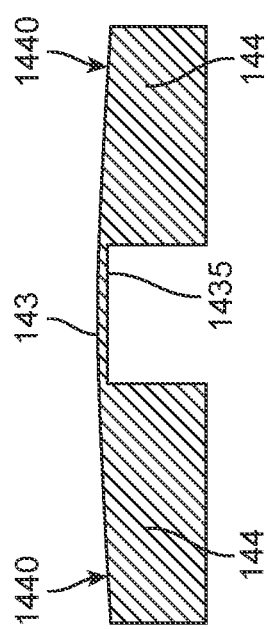
FIG. 3G is a cross-sectional view of a lens illustrating anterior optic geometry.
Figure 3H:
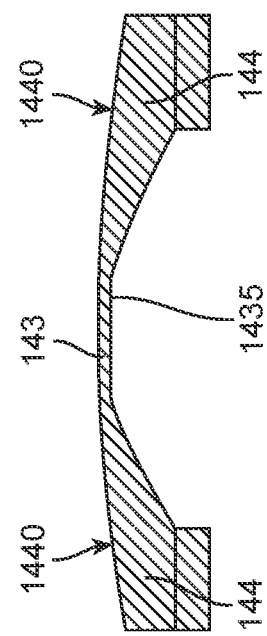
FIG. 3H is a schematic view of a dynamic membrane of the lens of FIG. 3G having an accommodated shape that is spherical.
Figures 1, 2, 3I, 3J:
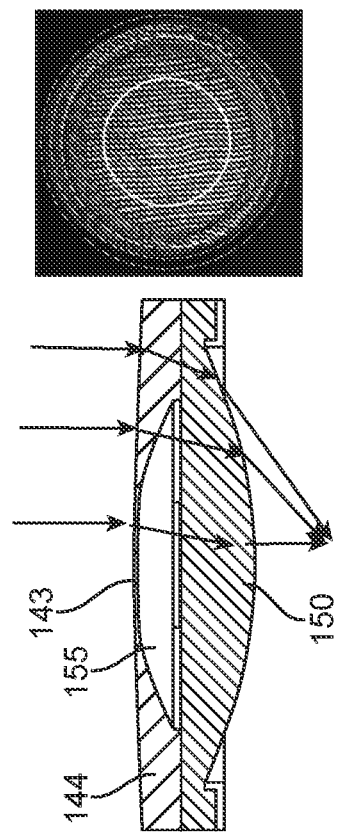

Other membrane designs can have an external shape upon shape change that is substantially spherical and has a single radius of curvature between the center of the membrane 143 and the peripheral edge of the membrane 143 (see FIGS. 3G-3H). The interior curvatures between the solid component of the lens and the liquid component form diverging lenses when the liquid component has an RI that is lower than the RI of the solid component affecting optical quality (see FIGS. 3I-1 and 3I-2). FIG. 3I-1 is an image of an anterior membrane using optical metrology equipment to assess optical quality of the lens having solid and liquid components where the liquid component has an RI that is lower than that of the solid component. The optical quality, often characterized as Modulation Transfer Function (MTF) can be measured using IOLA-Multifocal Diffractive (Rotlex, Israel). Parallel or substantially parallel lines shown in FIG. 3I-1 are indicative of good optical quality whereas a distorted image indicates poor optics. FIG. 3I-2 shows the lens of FIG. 3I-1 in schematic illustrating the light beams (arrows) passing through the membrane 143 and diverging upon entering the liquid component. Beams of light near the central region (solid line arrows) where no interior curvatures are present are impacted very little upon entering the liquid component. Beams of light where interior curvatures are present (dotted line arrows) form diverging lenses when the oil is under-matched thereby negatively affecting optical quality. The relative refractive index of the material can impact optical quality. In contrast, the interior curvatures between the solid component of the lens and the liquid component form no lens or converging lenses when the liquid component is index-matched or over-matched with respect to the RI of the solid component without impacting optical quality (see FIGS. 3J-1 and 3J-2). FIG. 3J-1 is an image of an anterior membrane using optical metrology equipment to assess optical quality of the lens having solid and liquid components where the liquid component has an RI that is index-matched to that of the solid component. FIG. 3J-2 shows the lens of FIG. 3J-1 in schematic illustrating the light beams (arrows) passing through the membrane 143 and then converging upon entering the liquid component. Beams of light near the central region where no interior curvatures are present as well as beams of light where interior curvatures are present form no lens when the oil is over-matched or form a converging lens when the oil is index-matched.

The IOLs described herein are preferably formed of materials configured for small incision implantation. The solid optical components of the lens can have elastomeric characteristics and can be made of soft silicone polymers that are optically clear, biocompatible, and in certain circumstances flexible having a sufficiently low Young's modulus to allow for the lens body to change its degree of curvature during accommodation. It should be appreciated that some solid optical components have a different Young's modulus than other solid optical components to provide different function to the lens (e.g. outward bowing of dynamic membrane 143 during accommodation compared to immovable static anterior optical portion 144 mitigating distortion during accommodation). Suitable materials for the solid optical component of the lens can include, but are not limited to silicone (e.g., alkyl siloxanes, phenyl siloxanes, fluorinated siloxanes, combinations/copolymers thereof), acrylic (e.g., alkyl acrylates, fluoroacrylates, phenyl acrylate, combinations/copolymers thereof), urethanes, elastomers, plastics, combinations thereof, etc. In aspects, the solid optical component of the lens is formed of a silicone elastomer, as described herein. The solid optical component can be formed of one or a combination of the materials described herein in which the liquid optical material described herein is fully encapsulated by the solid optical component. The solid optical component of a lens may include one or more regions that are configured to be in contact with and/or contain the liquid optical material. The liquid optical materials described herein can be specially formulated relative to the material of the solid optical component to mitigate lens instability and optimize optical quality. The liquid optical materials, sometimes referred to herein as an optical fluid, can include any of a variety of copolymers, including fluorosilicone copolymers and other liquid optical materials as described in PCT Application No. PCT/US2021/37354, filed Jun. 15, 2021, which is incorporated by reference herein in its entirety.

FIGS. 4A-4H show an implementation of a lens 100 having solid optical component and liquid optical material. The solid optical component can include a lens body 105 formed by any of a variety of components including the anterior optic 145 discussed above and the posterior static element 150. The sealed, fixed volume fluid chamber 155 defined by the lens body 105 can contain a fixed volume of the liquid optical material. The lens 100 can include an anterior optic having a central, dynamic zone or shape change membrane 143 surrounded by a static anterior optical portion 144 at a periphery of the anterior optic. The dynamic membrane 143 is configured to undergo a shape change whereas the static anterior optical portion 144 can be configured to resist or not to undergo a shape change. The static element 150, which can be a static lens, may not undergo a shape change as well. The cross-sectional geometry of the static anterior optical portion 144 and the dynamic membrane 143 can vary as discussed above. Where the cross-sectional thickness of the membranes appear uniform in the figure it should be appreciated that the thickness may vary as discussed elsewhere herein.

The equator region of the lens body 105 can include at least one shape deformation membrane 140 (best shown in FIG. 4E). The inner surfaces of the anterior optic 145, the dynamic membrane 143, the static anterior optical portion 144 of the anterior optic 145, the shape deformation membrane 140 and the static element 150 can collectively form the fixed volume, fluid chamber 155. The components defining the fluid chamber 155 can be the solid optical component whereas the fixed volume of material contained within the fluid chamber 155 can be the liquid optical material. The shape deformation membrane 140 can be positioned adjacent at least one force translation arm 115. As will be described in more detail below, movements of the force translation arm 115 causes movements of the shape deformation membrane 140 thereby deforming the liquid optical material and the fluid chamber 155 to cause a change in the shape of the dynamic membrane 143 of the lens body 105. The anterior optic 145 can be molded as a unitary piece of polymer material including the dynamic membrane 143, static anterior optical portion 144, shape deformation membrane 140, and force translation arms 115. Thus, the shape deformation membrane 140 and its associated force translation arm 115 can be molded together as a unitary part of the anterior optic 145. Any of a variety of the lens components may be molded together as a unitary piece or may be bonded together such as with glue or other bonding material. The lens can have minimal glued or bonded surfaces. In aspects, one or more of the lens components are coupled together by chemical connections rather than non-chemical bonding with glue.

Again with respect to FIG. 4A, the anterior optic 145 can be a flexible optic formed of an optically clear, low modulus polymeric material such as silicone, polyurethane, or flexible acrylic. The anterior optic 145 can include a static anterior optical portion 144 surrounding a central, dynamic membrane 143 configured to outwardly bow as discussed elsewhere herein. The dynamic membrane 143 can be positioned relative to the lens body 105 such that the optical axis A of the lens extends through the dynamic membrane 143. The anterior optic 145 can have a variable thickness. For example, the dynamic membrane 143 can have a reduced thickness compared to the static anterior optical portion 144. The thinner cross-sectional thickness of the dynamic membrane 143 compared to the cross-sectional thickness of the static anterior optical portion 144 can render it relatively more prone to give way upon application of a force on its inner surface. For example, upon an increased force applied against inner surfaces of the anterior optic 145 during deformation of the fluid chamber 155, the dynamic membrane 143 can bow outward along and coaxial to the optical axis A of the lens 100 while the static anterior optical portion 144 maintains its shape. The dynamic membrane 143 can be configured to give way due to pressure applied by the liquid optical material within the fluid chamber 155 onto the internal surface of the anterior optic 145 causing an outward bowing of the outer face (e.g., anterior face). Outer static anterior optical portion 144 of the anterior optic 145 can have a thickness greater than the inner dynamic membrane 143 of the optic 145 and can be more resistant to reshaping under such internal pressure applied by the liquid optical material in the fluid chamber 155. The outer static anterior optical portion 144 of the anterior optic 145 can provide distance vision correction even when the inner dynamic membrane 143 is reshaped for near vision.

The dynamic membrane 143 can have a substantially constant thickness such that it is a planar element. Preferably, the dynamic membrane 143 can have a variable thickness between its outermost edge and central region as discussed in more detail above and as shown in FIGS. 2B, 3A-3D. The dynamic membrane 143 can have a linear gradient thickness, curved gradient thickness, 2, 3 or more thicknesses with a step including radiused or right angles.

The dynamic membrane 143 can also include multiple materials, for example, materials configured to flex near a center of the dynamic membrane 143 and other materials configured to reinforce the optic zone and limit distortion. Thus, the dynamic membrane 143 of the anterior optic 145 can be formed of a material that is relatively more susceptible to outward bowing than the material of outer static anterior optical portion 144. The various regions of the optic 145 can be injection or compression molded to provide a relatively seamless and uninterrupted outer face. The material of the regions can be generally consistent, though the dynamic membrane 143 can have different stiffness or elasticity that causes it to bow outward farther than the static anterior optical portion 144.

The anterior optic 145 can be configured to have varied multifocal capabilities to provide the wearer of the lenses described herein with enhanced vision over a wider range of distances, for example, as described in U.S. Publication No. 2009/0234449, which is incorporated by reference herein in its entirety. The "optic zone" as used herein generally refers to a region of the lens body 105 that surrounds the optical axis A of the lens and is optically clear for vision. The "accommodating zone" as used herein generally refers to a region of the lens body 105 capable of undergoing shape change for focusing (e.g. the dynamic membrane 143). The optic zone is configured to have a corrective power although the entire optic zone may not have the same corrective power. For example, the dynamic membrane 143 and the static anterior optical portion 144 of the anterior optic may each be positioned within the optic zone. The dynamic membrane 143 may have corrective power whereas the static anterior optical portion 144 may not have corrective power. Or, for example, the diameter defined by the dynamic membrane 143 may have an optical power and the static anterior optical portion 144 may have a power that is greater or lesser than that of the dynamic membrane 143. The dynamic membrane 143 can be equal to or smaller than the overall optical zone can create a multi-focal lens. The accommodating zone of the lens body 105 can be equal to or smaller than the overall optic zone.

The shape deformation membrane 140 can extend along an arc length of the equator region of the lens body 105. The arc length can be sufficient, either individually or in combination with other shape deformation membranes 140, to cause a reactive shape change in the dynamic membrane 143 upon inward (or outward) movement of the deformation membrane 140. Movement of the shape deformation membrane 140 in a generally inward direction towards the optical axis A of the lens 100 during accommodation can cause outward flexure or bowing of the dynamic membrane 143 without affecting the overall optic zone diameter in any axis.

The shape deformation membrane 140 can have a flexibility such that it is moveable and can undergo displacement relative to the lens body 105, the static element 150, and the anterior optic 145. For example, the shape deformation membrane 140 can be more flexible than adjacent regions of the lens body 105 such that it is selectively moveable relative to the lens body 105 and the static anterior optical portion 144 of the anterior optic 145. The shape deformation membrane 140 can have a resting position. The resting position of the shape deformation membrane 140 can vary. In aspects, the resting position is when the shape deformation membrane 140 is positioned generally perpendicular to a plane parallel to the anterior optic 145 such that it has a cross-sectional profile that is vertically oriented, parallel to the optical axis A. The resting position of the shape deformation membrane 140 can also be angled relative to the optical axis A of the lens body 105. The shape and relative arrangement of the one or more side deformation membranes 140 provides the lens with a low force, low movement, high accommodative function.

The movement of the shape deformation membrane 140 can be a compression, collapse, indentation, stretch, deformation, deflection, displacement, hinging or other type of movement such that it moves in a first direction (such as generally toward an optical axis A of the lens body 105) upon application of a force on the shape deformation membrane 140.

The shape deformation membrane 140 lies adjacent or is coupled to or molded integral with a respective force translation arm 115. The one or more force translation arms 115 are configured to harness movements of one or more of the ciliary structures such that they are bi-directionally movable relative to the lens body 105 to effect accommodative shape change of the lens body 105. For example, and without limiting this disclosure to any particular theory or mode of operation, the ciliary muscle 18 is a substantially annular structure or sphincter. In natural circumstances, when the eye is viewing an object at a far distance, the ciliary muscle 18 within the ciliary body relaxes and the inside diameter of the ciliary muscle 18 gets larger. The ciliary processes pull on the zonules 20, which in turn pull on the lens capsule 22 around its equator. This causes a natural lens to flatten or to become less convex, which is called disaccommodation. During accommodation, the ciliary muscle 18 contracts and the inside diameter of the ring formed by the (ciliary ring diameter, CRD) ciliary muscle 18 gets smaller. The ciliary processes release the tension on the zonules 20 such that a natural lens will spring back into its natural, more convex shape and the eye can focus at near distances. This inward/anterior movement of the ciliary muscle 18 (or one or more ciliary structures) can be harnessed by the force translation arms 115 to cause a shape change in the lens body 105.

In aspects, as the force translation arm 115 is moved inwardly toward the optical axis A of the lens 100 due to ciliary muscle contraction, the force translation arm 115 abuts an outer surface of the shape deformation membrane 140 and applies a force against the outer surface. Thus, the contact between the shape deformation membrane 140 and the force translation arm 115 can be reversible contact such that upon ciliary muscle contraction the force translation arm 115 is urged against the outer surface abutting the membrane 140 and urging it inwardly. Upon ciliary muscle relaxation, the shape deformation membrane 140 returns to its resting position and the force translation arm 115 returns to its resting position. The elastomeric nature of the movable components (i.e. the dynamic membrane and/or the shape deformation membranes) can cause a return of the force translation arms 115 to their resting position. In aspects and as best shown in FIG. 4E, the shape deformation membrane 140 is coupled to or integral with its respective force translation arm 115. As with other aspects, upon ciliary muscle contraction the force translation arm 115 and shape deformation membrane 140 move in concert from a resting position to a generally inwardly-displaced position causing shape change of the dynamic membrane 143. Displacement of the force translation arm 115 and associated shape deformation membrane 140 applies a compressive force on the fluid chamber and in turn deforms the chamber causing the dynamic membrane 143 to bulge outward.

The inward motion of the force translation arm 115 and associated shape deformation membrane 140 can be coaxial to an axis that is substantially orthogonal or perpendicular to the optical axis A. Meaning, the angle between the axis of motion and the optical axis can be 90 degrees plus or minus about 1 degree, 2 degrees, 3 degrees, 4 degrees, up to about 5 degrees. It should be appreciated that a compressive force applied to the force translation arms 115 such as by a ciliary structure may result in radially inward motion that is not perfectly orthogonal to the optical axis A and that some degree greater than or less than 90 degrees is considered herein. The angle between the axis of motion of the deformation membrane 140 and the optical axis A can also be substantially non-orthogonal or non-perpendicular. For example, the deformation membrane 140 can be compressed along an axis that is non-orthogonal to the optical axis A.

The number and arc length of each deformation membrane 140 can vary and can depend on the overall diameter and thickness of the device, the internal volume, refractive index of the material, etc. Generally, the lens body has sufficient rigidity and bulk to the lens such that it can be handled and manipulated during implantation while the deformation membrane(s) 140 are sufficiently flexible to allow the force translation arms to change the shape of the fluid chamber 155. Depending on the overall diameter and thickness of the lens 100, the arc length of the shape deformation membrane 140 can be at least about 2 mm to about 8 mm. In aspects, the lens has a single shape deformation membrane 140 with an arc length of between about 2 mm to about 8 mm. The single shape deformation membrane 140 can be designed to move between about 10 µm and about 100 µm upon application of forces as low as about 0.1 grams of force (gf) to achieve at least a 1D, or 1.5D, or 2D, or 2.5D, or 3D change in the dynamic membrane 143. In aspects, the IOL can have two, opposing shape deformation membranes 140 each having an arc length that is between about 3 mm and about 5 mm. The shape deformation membranes 140 can be designed to move between about 25 µm and about 100 µm each upon application of about 0.25 g force to 1.0 g force achieve at least a 1D change in the dynamic membrane 143.

The shape deformation membranes 140 can move or collapse relative to the rest of the lens body upon application of a degree of compressive force. Generally, the IOL is designed such that very low forces (including the application of compressive force towards the optical axis A as well as the release of the compressive force) are sufficient to cause micron movements to cause sufficient diopter changes and with reliable optics. The compressive force applied to achieve outward movement of the dynamic membrane 143 of the lens body 105 to effect accommodation can be as low as about 0.1 grams of force (gf). In aspects, the compressive force applied can be between about 0.1 gf to about 5.0 gf or between about 0.25 gf to about 1.0 gf or between about 1.0 gf to about 1.5 gf. The movements of the deformable regions of the lens body 105 (e.g. shape deformation membrane 140) relative to the central portion of the lens body 105 (e.g. dynamic membrane 143) in response to the compressive forces applied to achieve accommodation can be as small as about 50 µm. The movements of the shape deformation membrane 140 of the lens body relative to the dynamic membrane 143 in response to the compressive forces applied can be between about 50 µm to about 500 µm, between about 50 µm to about 100 µm, between about 50 µm to about 150 µm, or between about 100 µm to about 150 µm. The ranges of compressive forces applied (e.g. about 0.1 gf to about 1 gf) that result in these ranges of movement in the shape deformation membrane 140 (e.g. 50 µm-100 µm) can provide the devices described herein with an accommodating capability that is within a dynamic range of greater than at least ±1D and preferably about ±3 diopters (D). In aspects, the power is between ±4D and ±6D for about 100-150 µm movement. The devices described herein can have an accommodating range that is at least ±1D for about 100 µm movement of the shape deformation membrane 140 and about a compressive force of at least 0.25 gf applied to the shape deformation membrane 140 in a substantially inward direction towards the optical axis A. In aspects, the devices can have an accommodating range that is at least ±1D for about 50 µm movement and at least about 1.0 gf. In aspects, the devices can have an accommodating range that is at least ±3D for about 100 µm movement and at least about 1.0 gf. In aspects, the devices can have an accommodating range that is at least ±3D for about 50 µm movement and at least about 0.1 gf.

The micron movements described herein can be asymmetrical micron movements (e.g. from one side of the device) or can be symmetrical micron movements from opposing sides of the device or evenly distributed around the device relative to the optical axis. Whether the micron movements are asymmetric or symmetrical, the outward bowing of the dynamic membrane 143 achieved can be substantially spherical. The micron movements described herein also can be a total collective movement of the shape deformation membranes 140. As such, if the lens 100 includes a single shape deformation membrane 140, that single membrane is capable of desired micron movement (e.g. 50 µm-100 µm) to achieve desired dioptric change (e.g. at least 1D to about 3D change). If the lens 100 includes two shape deformation membranes 140, the membranes together are capable of the achieving between 50 µm-100 µm movement to achieve the at least 1D dioptric change. The dioptric change achieved by the devices described herein can be at least about 1D up to approximately 5D or 6D change. In aspects, the dioptric change can be between 7D and 10D, for example, for patients having macular degeneration.

As mentioned above and still with respect to FIGS. 4A-4G, the lens body 105 can include a static element 150. The static element 150 and the anterior optic 145 can be located opposite one another along the optical axis A of the lens 100. The static element 150 can be positioned outside the lens body 105 such that the flat surface 151 forms the inner surface facing the fluid chamber 155 of the lens body 105 and the curved surface 152 is in contact with the fluid of the eye. Alternatively, the static element 150 can be positioned inside the lens body 105 such that the flat surface 151 is in contact with the fluid of the eye and the curved surface 152 forms the inner surface facing the fluid chamber 155 of the lens body 105.

The static element 150 can be optically clear and provide support function without affecting the optics of the lens 100. As such, the static element 150 can have zero power and can form a posterior support to the lens body 105. The static element 150 can be formed of silicone, urethane, acrylic material, a low modulus elastomer, or combinations thereof. The static element 150 can be or include a static optic to correct to emmetropic state, or can be of an appropriate power for an aphakic patient (usually ±10D to ±30D). Thus, the static element 150 can have no optical power up to about ±30D. If the lens 100 is being used in conjunction with a separate capsular lens (e.g. as a "piggyback" lens), the power can be in the range of about −5D to about +5D to correct for residual refractive or other optical aberrations in the optical system of the eye. The static element 150 can be plano-convex, convex-plano, convex-convex, concave-convex or any other combination. The static element 150 (or the lens positioned posteriorly) can be a toric lens, spherical lens, aspheric lens, diffractive lens or any combination of both, for example, in order to reduce or compensate for any aberrations associated to the flexible lens. The relative refractive indices of the static element 150 and the fluid surrounding it (whether that is the fluid of the eye or liquid optical material within the fluid chamber 155) will determine the power of the static element 150 for any given shape.

The lens 100 can include any of a variety of combinations of reinforcements and/or supports to provide mechanical stability to the assembled lens 100. For example, the reinforcements may be in the peripheral regions of the anterior lens 145 and/or the static element 150. The reinforcements can be either optically clear or opaque. The reinforcing structures may be formed of a rigid polymer, including but not limited to silicone, polyurethane, PMMA, PVDF, PDMS, polyamide, polyimide, polypropylene, polycarbonate, etc, or combinations thereof. Other regions of the lens 100 can include one or more reinforcements or supports as well. In aspects, the one or more supports can be positioned external to the fluid chamber 155 such that the supports surround at least an outside portion of the lens body 105. For example, the external support can be a generally annular element extending around a perimeter of the lens body 105 and have a central opening through which at least the dynamic membrane 143 of the anterior optic 145 is aligned such that the dynamic membrane 143 is available for outward deformation.

In aspects, the lens 100 includes one or more internal supports located within one or more regions of the lens 100 that are configured to mechanically isolate the optical elements (anterior and posterior) from stresses imparted by another part of the lens, such as the stabilization system 120 and/or the force translation arms 115, to limit optical distortion. Generally, the material and/or structure of the internal supports provides enough rigidity to mechanically isolate the optical elements, particularly when the lens 100 is placed under stress imparted by stabilization system 120 or the force translation arms 115. The internal supports can be immovable features (meaning a feature not involved in accommodation) that are configured to mechanically isolate and thereby prevent or mitigating optical distortions even during movement of other lens components (e.g., a haptic, force translation arm, etc.). They provide support by ensuring they impart no shape change to the optical portions of the device such as the dynamic membrane 143 or the anterior optic 143 when the lens is placed under some sort of force or stress. The strength of the internal supports relative to other portions of the lens 100 such as the shape deformation membrane 140 and the dynamic membrane 143 provides increased durability during manipulation and handling of the lens during insertion.

As will be described in more detail below, the internal supports can be positioned within or facing the fluid chamber 155 of the lens body 105 and/or embedded in one or more regions of the solid optical components. The one or more internal supports can be thickened portions on an interior side of or embedded within the outer, static anterior optical portion 144 of the anterior optic 145. The one or more internal supports can also be separate components coupled to or located within one or more regions of the lens. The one or more internal supports can be coupled to and/or embedded inside the static anterior optical portion 144 of the anterior optic 145. The internal supports can be formed of a material (or materials) that is harder, thicker and/or more rigid than the shape deformation membrane 140 or the dynamic membrane 143 of the anterior optic 145 to prevent inadvertent movements of the moving parts of the device. Alternatively, the internal supports may be made of the same material as the shape deformation membrane 140 or the dynamic membrane 143 of the anterior optic 145 and accomplish the mechanically isolating function due to the geometry of the support structure. The support can be formed of a rigid polymer, including but not limited to silicone, polyurethane, PMMA, PVDF, PDMS, polyamide, polyimide, polypropylene, polycarbonate, etc., or combinations thereof. For example, the internal support can be a combination of multiple silicones or silicone with a rigid or semi-rigid skeletal insert.

The internal supports can be formed in any of a variety of configurations, sizes, shapes, and/or materials. The internal supports can include a material embedded within the material of another portion of the anterior optic 145. The cross-sectional views of FIGS. 4E-4F show embedded internal supports 110e within the outer, static optical portion 144. The cross-sectional view of the lens shown in FIG. 4G has the upper surfaces of the anterior optic 145 including the central, dynamic membrane 143 cut-away revealing the fluid chamber 155 and a plurality of connecting columns 112. These connecting columns 112 can be part of the anterior optic 145 or made from the same material as the anterior optic 145. These connecting columns 112 can be part of the posterior optic 150. The connecting columns 112 can be used to bond the anterior optic 145 to the posterior optic. In some implementations, these distinct columns of material can provide support for the optics of the lens. The columns 112 and the embedded supports 110e may be collectively referred to herein as simply internal supports 110.

Again with respect to FIGS. 4E, 4F, and 4G, the embedded internal supports 110e can include one or more stiffeners or other component or material(s) embedded within the polymer of the anterior portion of the lens body 105. As an example, the embedded supports 110e can be a rigid silicone material embedded in the softer silicone material of another solid portion of the lens. The embedded supports 110e can be any of a variety of materials provided herein including, but not limited to, silicones, polyurethanes, PMMA, PVDF, PDMS, polyamide, polyimide, polypropylene, polycarbonate, etc., or combinations thereof. The embedded internal supports 110e can be relatively planar elements that lie generally parallel to the central, longitudinal plane of the lens 100. An outer region of each support 110 can be positioned adjacent to the equator region of the lens body 105 and extend inward a distance towards the dynamic membrane 143 of the anterior optic 145. The outer region of the support 110e can be coupled to or integral with the equator region of the lens body 105 or the outer region of the support 110e can be spaced away from the equator region. The support 110e can extend along a length of the peripheral region of the static anterior optical portion 144, but be spaced away from the equator region near where the deformation membrane 140 extends along an arc length of the equator region (see FIG. 4G). This spacing away from the deformation membrane 140 provides tolerance such that the deformation membrane 140 does not prematurely abut or contact the support 110e or the outer static anterior optical portion 144 during inward accommodative movements.

Figure 4A:
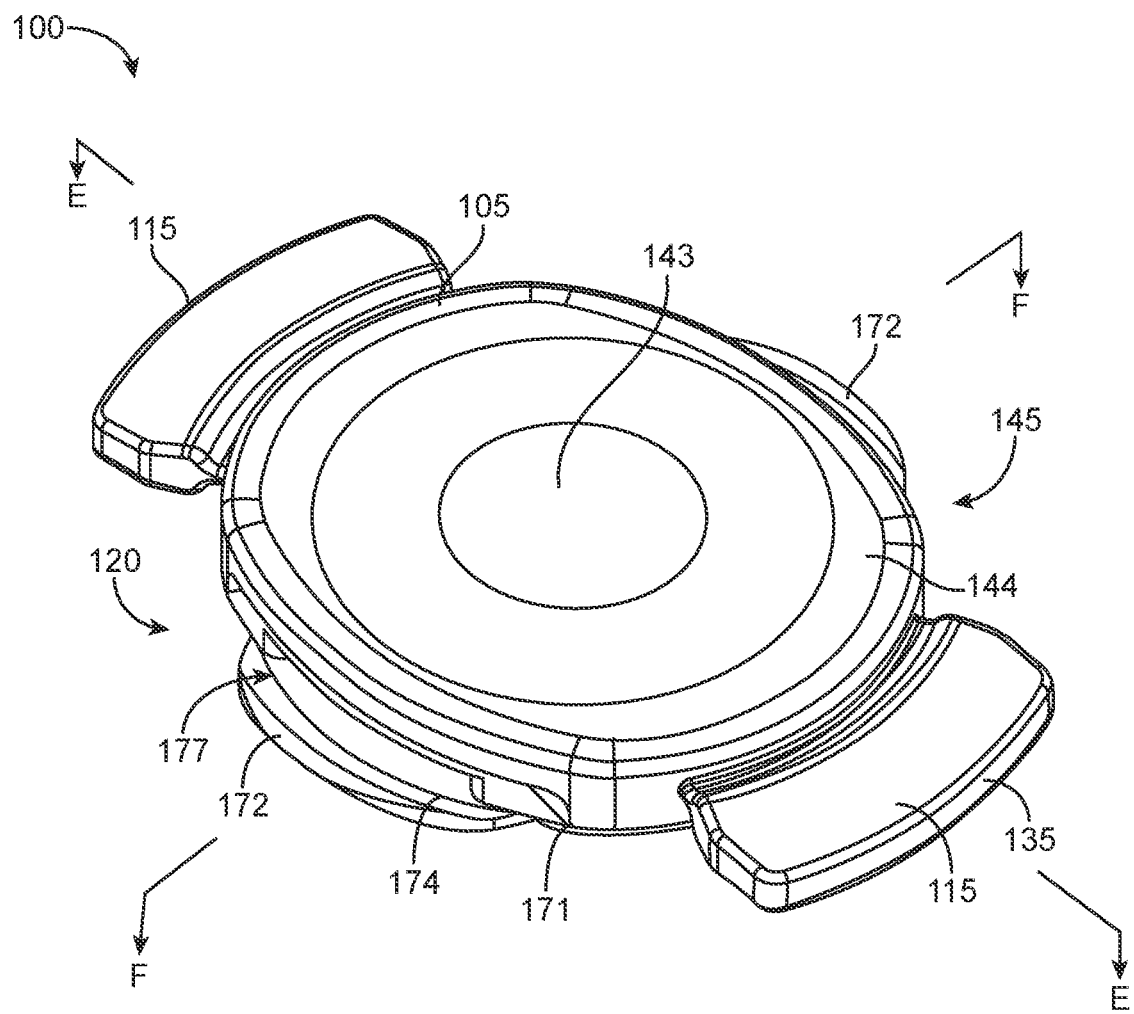
FIG. 4A illustrates a perspective view of an implementation of a lens.
Figure 4B:
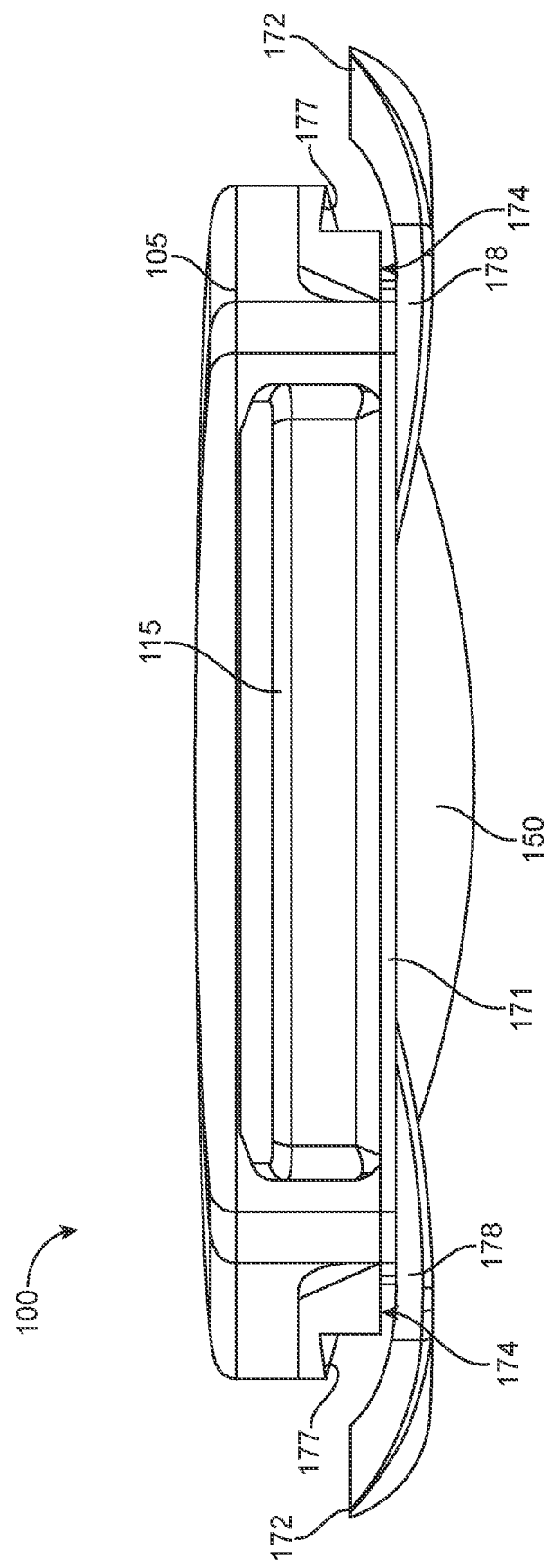
FIG. 4B is a side view of the lens of FIG. 4A.
Figure 4C:
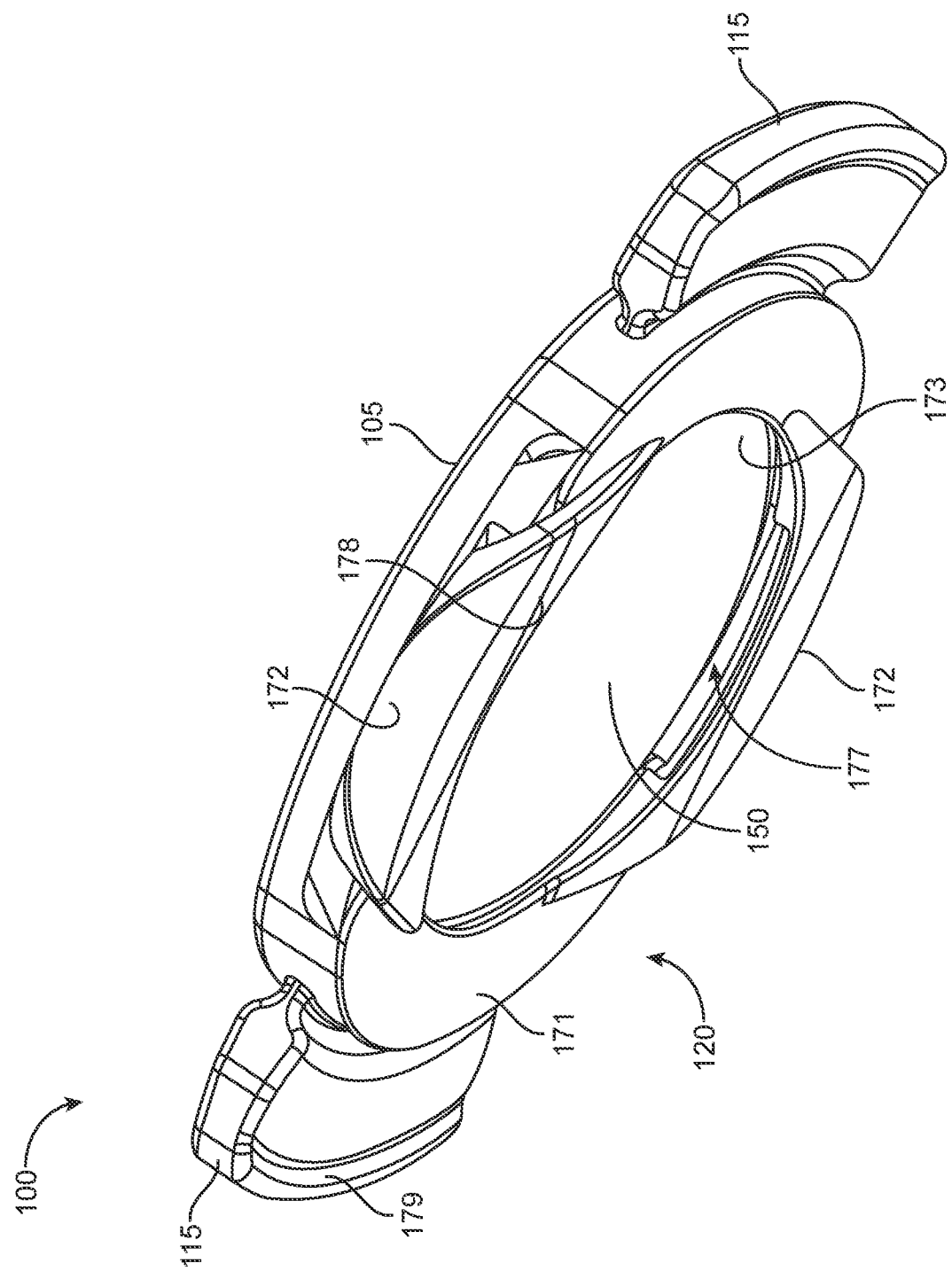
FIG. 4C is a posterior perspective view of the lens of FIG. 4A.
Figure 4D:
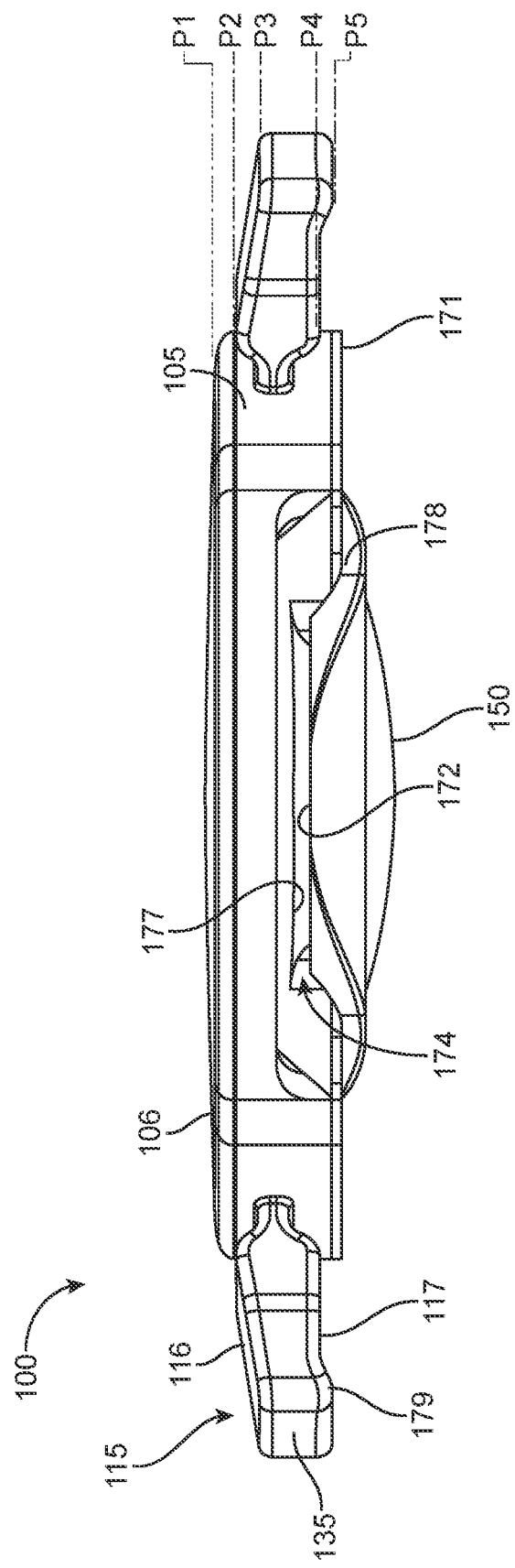
FIG. 4D is a side view of the lens of FIG. 4A.
Figure 4G:
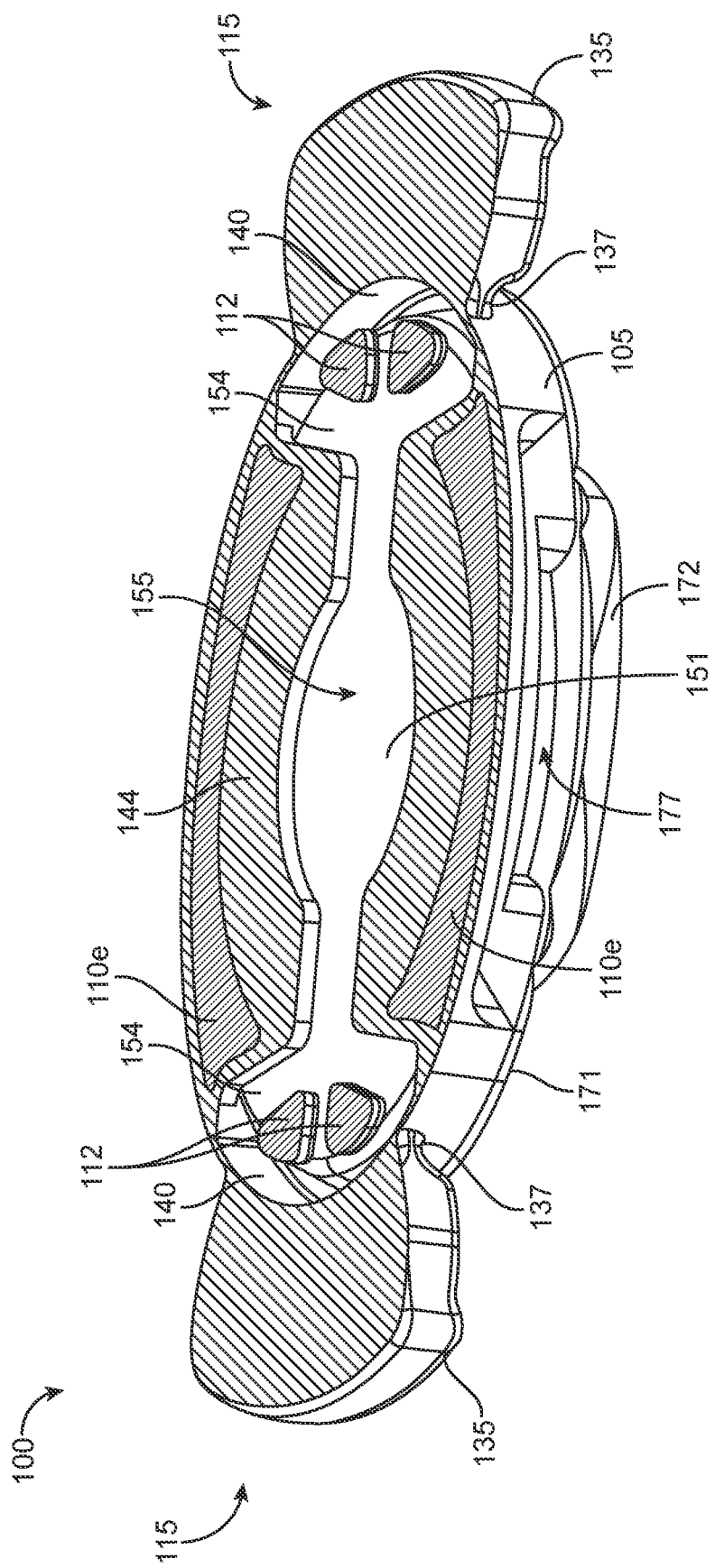
FIG. 4G is cross-sectional view of the lens of FIG. 4A showing support structures of the lens.

The connecting columns 112 can be relatively narrow and distinct structures formed of reinforcing material(s) that are integral with, coupled to, and/or otherwise positioned near a peripheral region 154 of the anterior optic 145. FIG. 4G illustrates regions of connecting columns 112 near the location of each deformation membrane 140. The connecting columns 112 can be spaced a distance inward from each deformation membrane 140. Their positioning relative to the deformation membrane and their relatively narrow shape enables movement of the membrane 140 without risk of contact or disruption of the deformation. FIG. 4G shows each region of connecting columns 112 has a pair of connecting columns 112 spaced a distance away from one another as well as a distance away from the deformation membrane 140 and away from the static anterior optical portion 144 with embedded internal supports 110e. A first embedded internal support 110e can extend along the arc length between each of the deformation membranes 140 and a second embedded internal support 110e can extend along the arc length between the deformation membranes 140 on the opposite side of the lens body 105. Although FIG. 4G shows each region of connecting columns 112 has two connecting columns 112, there can be just one connecting column 112 near each deformation membrane 140 or more than two connecting columns 112 near each deformation membrane 140. Generally, the connecting columns 112 can be narrower than the embedded supports 110e. The embedded internal supports 110e can extend along a greater arc length than each of the distinct connecting columns 112 such that they are generally longer, wider, and flatter than the connecting columns 112. However, the embedded supports 110e can also take on a more distinct shape within the material of the static anterior optical portion 144 so that they too form narrow, distinct points of support rather than an elongate support section.

The distribution and spacing of the connecting columns 112 relative to the shape deformation membrane 140 can minimize their contact with the moving parts of the lens whether near the static zone of the lens body 105 or the central region of the lens body 105. The shape of the connecting columns 112 can also minimize or limit contact between the connecting columns 112 and the shape deformation membrane 140. For example, the outer region of the connecting columns 112 can be beveled near the equator region such that the bevel allows for inward movement of the shape deformation membrane 140 while avoiding contact between the membrane 140 and the outer perimeter of the supports. The bevel can be a single bevel having an angle that is between about 10-80 degrees. It should be appreciated that the outer region of the one or more supports need not include a bevel. Contact between the shape deformation membrane 140 and the one or more connecting columns 112 can be avoided in other ways aside from incorporating a bevel. For example, the one or more connecting columns 112 can be spaced a distance away from the shape deformation membrane 140 (e.g. along the perimeter and/or away from the perimeter) to avoid contact. The connecting columns 112 can also have a dimension between the outer regions to their inner regions such that they extend a distance towards the center of the lens body providing stability and support, but generally stop short of the central, dynamic membrane 143 of the anterior optic 145. In some implementations, such as shown in FIG. 4G, the connecting columns 112 take the place of the static anterior optical portion 144 at the location along the equator of the lens body 105 near the deformation membrane 140. The static anterior optical portion 144 thus, only extends around the equator in the section of the lens body 105 between the location of the deformation membranes.

The connecting columns 112 can have different shapes and sizes to provide an overall shape to the fluid chamber 155. In an implementation, the support columns 112 can include distinct, narrow columns of material extending anterior-to-posterior through the lens that are interspersed between larger connecting columns 112. The narrow columns of material can be positioned inside the optic zone of the lens while the larger internal supports can be positioned outside the optic zone and each can be located away from movable solid components. The large connecting columns positioned outside the optic zone collectively can provide an overall shape to the fluid chamber 155 containing the liquid component. The distinct, narrow columns of material interspersed between the larger internal support columns can provide support within these large hallways or channels of the fluid chamber 155 formed by the larger support columns.

As mentioned, the lens body 105 can include a sealed, fixed volume fluid chamber 155 collectively formed by the inner-facing surfaces of the shape deformation membrane 140, the anterior optic 145, and the static element 150 and containing a fixed volume of an liquid optical material. The inner-facing surfaces of the one or more inner connecting columns 112 as well as the static anterior optical portion 144 (with the embedded supports 110e) and the inner-facing surface of the dynamic membrane 143 of the anterior optic 145 also form part of the fluid chamber 155. Thus, the distribution, size, shape and number of the one or more connecting columns 112 and the static anterior optical portion 144 impacts the overall shape of the fluid chamber 155 (see FIG. 4G).

Regardless the configuration, the internal supports 110 (both embedded supports 110e and connecting columns 112) can limit efficiency-sapping lens movements in regions of the lens 100 other than where accommodative movements are desired. The internal supports 110 function to focus all ciliary-induced pressure toward the central, dynamic membrane 143. The internal supports 110 mechanically isolate dynamic areas of the lens 100 and structurally reinforce non-dynamic areas of the lens 100 thereby focusing the shape change only where desired for accommodation—the side deformation membrane 140 via movements of the force translation arm 115 and the dynamic membrane 143 from the increased pressure within the fluid-filled chamber 155. The geometry and rigidity of the internal supports 110 serves to mechanically prevent other lens regions from deforming under the increased internal pressure of the fluid-filled capsule.

The internal supports 110 can be formed of any of a variety of materials or combination of materials that can be opaque or clear, but are generally more rigid than the moveable parts of the lens 100. In aspects, each solid component of the lens 100 is formed of the same material, which provides advantages from a manufacturing standpoint. The material of the various solid components may be the same (e.g., silicone), but the mechanical properties of the various solid components may be unique depending on what function the component performs for the lens (i.e. shape change or force transfer or centering and stabilization). One solid component of the lens may be more rigid than another component of the lens (e.g., the internal supports 110 compared to the peripheral membrane 140), but both solid components may be the same material. The more rigid solid component may be more rigid due to that component's geometry and dimensional differences compared to the less rigid solid component. As such, the internal supports 110 and the membranes 140, 143 can be formed of the same silicone material, but because the membranes 140, 143 have a significantly decreased thickness compared to the internal supports 110 the membranes 140, 143 are easily deformed upon application of a compressive force whereas the internal supports 110 are not easily deformed. In some implementations, the internal supports 110 can be a silicone elastomer (e.g., silicone PDMS 70-90 shoreA) and the membranes 140, 143 can be a silicone elastomer (e.g., silicone PDMS 20-50 shoreA). Additionally, the internal supports 110 can include a geometry that imparts a higher rigidity and stiffness relative to the membranes 140, 143.

The liquid optical material contained within the fluid chamber 155 can be a non-compressible liquid optical material and the volume of the fluid chamber 155 can be substantially identical to the volume of liquid optical material. As such, the liquid optical material contained within the chamber 155 does not cause significant outward bowing of either the dynamic membrane 143 or the deformation membrane 140 in the resting state when no substantial outside forces are applied to the lens 100. In aspects, the fluid chamber 155 can be slightly overfilled with liquid optical material such that the dynamic membrane 143 has some outward bowing at rest. A small degree of resting outward bowing in the dynamic membrane 143 can reduce optical artifacts in the lens. However, no matter how much resting outward bowing is present in the dynamic membrane 143, the membrane 143 can still undergo additional outward bowing upon application of compressive forces on the shape deformation membrane 140 to provide accommodation. The pressure inside the fluid chamber 155 can be substantially equal to the pressure outside the fluid chamber 155. Because the liquid optical material in the fluid chamber 155 is non-compressible its shape deforms along with the shape of the chamber 155. Deformation of the chamber 155 in one location (e.g. micrometer inward movements of the shape deformation membrane 140) causes the non-compressible liquid optical material contained within the fixed-volume fluid chamber 155 to press against the inner-facing surfaces forming the fluid chamber 155. A reactive deformation of the fluid chamber 155 occurs in a second location to create sufficient accommodating change. The dynamic membrane 143 of the anterior optic 145 is configured to bow outward upon application of a force (e.g. due to relative thickness and/or elasticity) compared to other parts of the anterior optic 145 such as the static anterior optical portion 144. Thus, inward movement of shape deformation membrane 140 urges the liquid optical material to deform along with the chamber 155 and press against the inner-facing surface of the anterior optic 145. This results in outward bowing and reshaping of the outer surface of the dynamic membrane 143 to cause the accommodative portion of the optic zone to become more convex increasing the power of the lens 100. As discussed above, the internal supports 112, 110e provide sufficient stability to the lens body 105 so that application of the compressive forces on the shape deformation membrane 140 causes the micrometer movements with minimal distortion of the optics.

The liquid optical material contained within the fluid chamber 155 of the lens body 105 remains substantially within the optic zone during rest in both the unaccommodated, resting state and during accommodation. The liquid optical material remains within the lens body 105 and can contribute to the accommodative shape change of the dynamic membrane 143 by deforming in shape along with the deformation of the shape of the fluid chamber 155. It should be appreciated that this shape change of the dynamic membrane 143 can occur without actual flow of the liquid optical material within the fluid chamber 155, for example, from one part of the chamber to another. Rather, a force being applied on the shape deformation membrane 140 deforms the fluid chamber 155 in a first region that can cause a reactive deformation of the fluid chamber 155 in at least a second region. The fluid chamber 155 has a fixed volume and is deformable. The liquid optical material contained within the fluid chamber 155 changes shape along with and depending on the shape of the fluid chamber 155. Inward deformation of one or more portions of the chamber 155, for example, movement of the shape deformation membrane 140 near the static zone of the lens body 105, can cause a reactive outward deformation of another portion of the chamber 155, for example, outward bulging of the dynamic membrane 143 of the anterior optic 145, due to the non-compressible liquid optical material inside the fluid chamber 155 pressing against its inner surface. The liquid optical material need not flow between separate chambers of the IOL, but rather the liquid optical material can change shape along with the changing shape of the fluid chamber 155 to cause the accommodative portion of the optic zone of the anterior optic 145 to bow outward and increase the power of the IOL 100. As described elsewhere herein, very small movements of the force translation arms 115 (or single force translation arm 115 in the case of an asymmetric mechanism) result in immediate, small movements in the shape deformation membrane 140 to change the shape of the dynamic membrane 143 and sufficient dioptric change. Whether these very small movements are symmetrical due to at least a pair of opposing force translation arms 115 or asymmetrical due to a single force translation arm 115, the outward bowing of the dynamic membrane 143 that is achieved is spherical and symmetrical.

The shape deformation membrane 140 is sensitive to small forces imparted on the lens body 105. This is useful in providing accommodative changes upon ciliary muscle movements. However, this can cause power changes with undesirable optical consequences if the liquid optical material migrates away from the fluid chamber 155, for example, into the surrounding solid optical components 153. As discussed elsewhere herein, it is preferred that the liquid optical material be chemically dissimilar enough to prevent miscibility with the solid optical components 153 it comes into contact with. For example, if the liquid optical material is a silicone oil and the sealed chamber 155 is defined by solid optical components 153 formed of a chemically similar silicone elastomer like polydimethylsiloxane (PDMS), the silicone oil and silicone elastomer are miscible. The oil tends to enter into the silicone elastomer causing an unintended optical power change in the lens. The surface curvatures of the lens body would decrease (less convex or more concave) thereby reducing the power of the lens and providing insufficient optical power to the patient. This also reduces the ability of the lens to undergo sufficient shape change when necessary at the time of accommodation. Even minor changes of the internal pressure can result in substantial undesirable changes to the optical power of the lens.

Again with respect to FIGS. 4A-4H, the lens 100 can include one or more force translation arms 115 configured to move back and forth relative to the lens body 105 to cause the dioptric changes described elsewhere herein. The lenses described herein are particularly suited to harness the movements of the ciliary body applied directly onto the force translation arms 115 positioned against the ciliary structures into shape change of the lens. The force translation arms 115 are configured to harness and translate forces applied by the ciliary structures into the shape changes of the movable parts of the lens body 105 described above. Each force translation arm 115 can include an outer, contact portion 135 and an inner region 137 operatively coupled to a perimeter or equator region of the lens body 105 (see FIG. 4E). Inner regions 137 of each force translation arm 115 can be integral with, positioned in contact with, or adjacent the shape deformation membrane 140 such that the force translation arm 115 can move relative to the relaxed, shape deformation membrane 140. For example, the force translation arm 115 can be spaced away from the membrane 140 during rest, moved inward during accommodation to abut against the membrane 140 urging the membrane 140 inward, and then upon release of force during disaccommodation move away from the membrane 140 to release the membrane 140 from the inward, deforming force. As such, the inner region 137 of the force translation arm 115 can come into reversible contact with the shape deformation membrane 140 depending on whether an accommodating force is applied by the surrounding eye tissue. Alternatively, the inner region 137 of each force translation arm 115 can be physically coupled to or integral with the shape deformation membrane 140 such that the force translation arm 115 and the membrane 140 move in concert with one another.

In aspects, the inner region 137 of the force translation arm 115 can have a cross-sectional thickness taken along a plane between an anterior surface of the lens body 105 and the posterior surface of the lens body 105 that is narrower than a cross-sectional thickness of the equator region of the lens body 105 taken along the same plane. This can allow for the inner region 137 of the force translation arm 115 to displace the deformation membrane 140 a distance inward without abutting against the regions of the equator not intended to be deformed. It should be appreciated however, that the cross-sectional thickness of the inner region 137 of the force translation arm 115 need not be narrower. The outer contact portion 135 of the force translation arms 115 can, but need not, have a larger cross-sectional thickness than the inner region 137. It should be appreciated, however, that the outer contact portion 135 of the force translation arms 115 can also have the same cross-sectional thickness as the inner region 137. The outer contact portion 135 can also have rounded or curved contours.

Figure 4H:
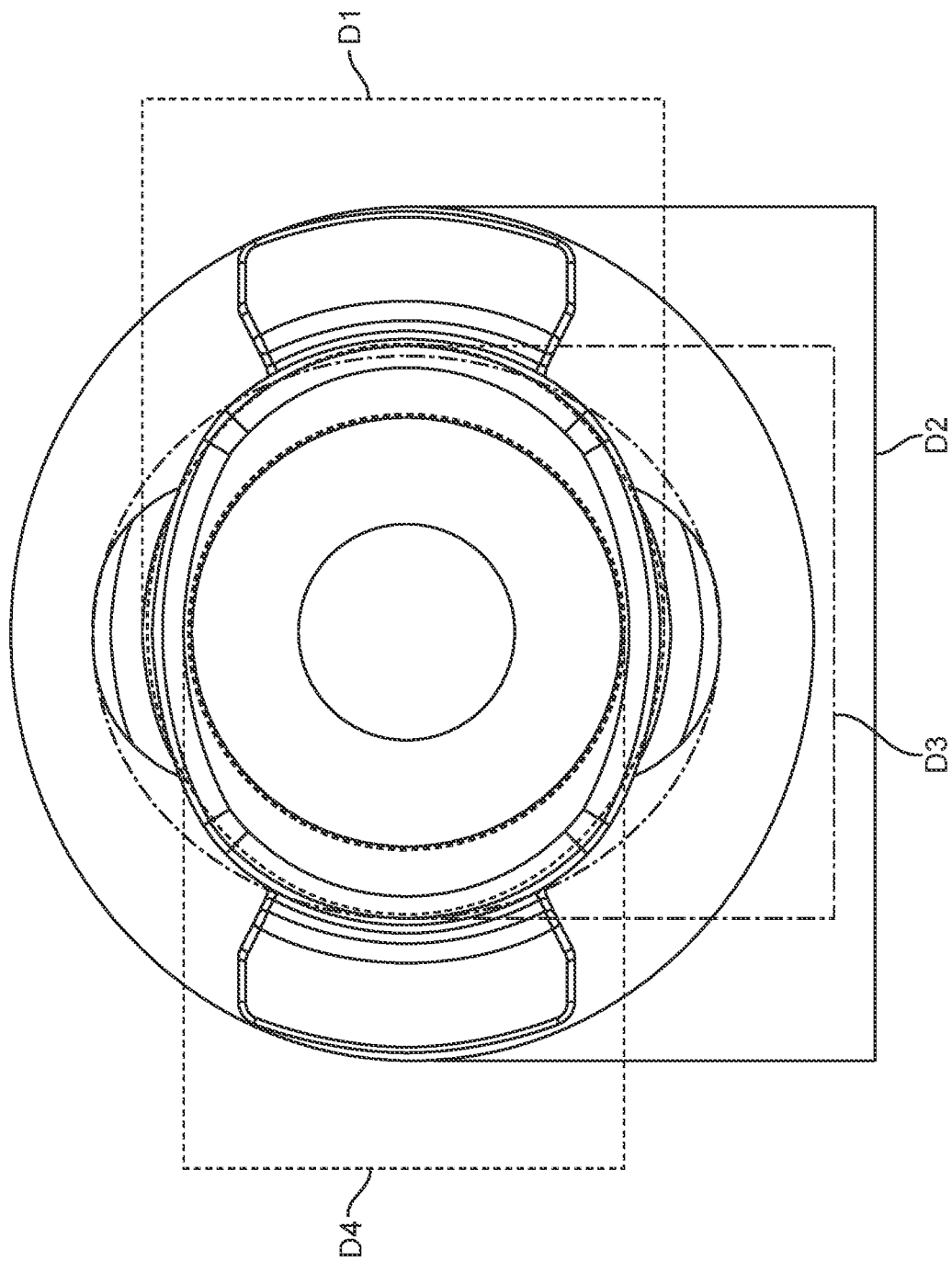
FIG. 4H is a top plan view of the lens of FIG. 4A showing diameters of different components of the lens.

The force translation arms 115 project beyond the equator of the lens body 105 defining a first outer diameter D1 so that the outermost edge of the force translation arms 115 define a second outer diameter D2 that is substantially equal to or less than an inside diameter of the ciliary muscle (see FIG. 4H). The second outer diameter D2 can also be slightly oversized relative to the inside diameter of the ciliary muscle. The first outer diameter D1 of the lens body 105 is smaller than the second outer diameter D2 of the force translation arms 115. In an implementation, the first outer diameter D1 can be between about 5.0 mm and about 9.0 mm and the second outer diameter D2 can be between about 8.5 mm and 13.5 mm. The first outer diameter D1 can be about 6.5 mm and the second outer diameter D2 can be between about 10.2 mm and 11.1 mm.

The force translation arms 115 of the lenses described herein are designed to contact ciliary tissues providing substantially non-circular outer perimeter surface. Thus, the area of contact between the lens and the surrounding tissues is far less than, for example, lenses designed to be fully implanted within the capsular bag. Capsular bag lenses generally have 360 degree contact with the bag to help support the structure of the bag and maintain distance between the anterior and posterior segments of the bag. Each force translation arms 115 of the lenses described herein can have between about 30 degree up to about 120 degree contact with the ciliary tissues. For a lens with two force translation arms 115, this results in between about 60 degree up to about 240 degree contact between the lens and the ciliary tissues. In some implementations, each force translation arm 115 of the lens has about 90 degree contact with the ciliary tissues providing only about 180 degree contact between the lens as a whole and the surrounding ciliary tissue. The outer contact portion 135 of the force translation arms 115 can provide contact with the surrounding ciliary tissues that is less than about 240 degrees, about 210 degrees, about 180 degrees, about 150 degrees, about 120 degrees, about 90 degrees, down to a minimum of about 60 degrees of outer contact. The force translation arms 115 together can have a minimum contact along an arc of 2.5 mm and a maximum contact along an arc of about 6 mm based on a ciliary process diameter of about 10.5 mm, such that the contact made by the force translation arms 115 as a whole can be about one third of the ciliary process.

The outer contact portion 135 of the force translation arms 115 can be designed to contact ciliary tissues while minimizing contact with the posterior side of the iris. Bulkiness in this region of the posterior chamber can increase the risk for glaucoma in patients. In an implementation, the anterior corners of the force translation arms 115 can be beveled or taper such that the anterior-to-posterior thickness of the arm 115 decreases towards the outermost periphery compared to more central regions of the arms to minimize contact between the arms 115 and the iris (see FIG. 4D). The force translation arms 115 can have an anterior-facing surface 116. The entire anterior-facing surface 116 of the force translation arms 115 can remain below or posterior to a plane P1 of the anterior-facing surface 106 of the lens body 105. The bevel of the anterior corners of the force translation arms 115 can result in the outermost periphery of the arms 115 lying within a plane P3 that is posterior to a plane P2 of an inner region of the arms 115 as shown in FIG. 4D and both planes P2, P3 can lie posterior to the plane P1 of the anterior-facing surface 106 of the lens body 105. The arrangement of the lens body 105 and the arms 115 minimizes contact of the outermost perimeter regions of the IOL with the iris while maximizing the size of the lens body 105 near the inner regions of the IOL for shape change and accommodation. The outer contact portions 135 can have a relatively thin anterior-to-posterior dimension. The combination of a thin outer contact portions 135 and small degree of contact around the ciliary body minimizes the overall surface area of contact between the lens and the eye tissue. The contact region between the lens and the ciliary tissues can have an anterior-to-posterior thickness that is no more than about 0.4 mm to about 0.6 mm. The contact region between the lens and the ciliary tissues can have an arc length that is no more than about 2.5 mm to about 6.0 mm. Despite this smaller contact region compared to, for example, in-the-bag style lenses, the lenses describe herein are capable of achieving a minimal level of shape change.

The contact portions 135 of the force translation arms 115 can incorporate features that improve their connection with one or more of the ciliary structures without causing damage. Generally, the contact portions 135 avoid piercing or causing trauma to the ciliary structures. In aspects, the contact portions 135 can interfere with the ciliary structures while providing an atraumatic surface to engage adjacent eye tissues such that movement can be transferred without causing trauma to the tissues themselves. The outer contact portion 135 can also be molded to have one or more concavities, indentations, grooves, teeth, combs, or other surface features to improve, for example, contact and/or interdigitation with eye tissues such as the ciliary process or zonular process. FIG. 4D shows the lower surface of the force translation arms 115 can have a contoured shape or surface feature such as ridge 179. The arms 115 can have a posterior-facing surface 117. An inner region of the posterior-facing surface 117 that is nearer to the equator of the lens body 105 can be substantially planar so as to lie substantially within a plane P4. The ridges 179 can be positioned near an outer region of the posterior-facing surface 117 of the arms 115 that is farther away from the equator of the lens body 105. The ridges 179 can project posteriorly relative to the planar inner region of the posterior-facing surface 117 within a plane P4. The feature improves contact between the arms 115 and the surrounding tissues.

The lens 100 can be implanted such that the contact portion 135 of the force translation arms 115 is either in resting contact or readily in contact upon contraction of the ciliary muscle 18 with at least one of the ciliary structures (i.e. zonules, ciliary processes, ciliary muscle, and/or ciliary body) to drive shape change of the optics during accommodation and disaccommodation. In a preferred implementation, the lens 100 is implanted such that the contact portion 135 of the force translation arms 115 lies in resting contact or ready contact with the ciliary body apex. In another preferred implementation, the lens 100 is implanted such that the contact portion 135 of the force translation arms 115 lies in resting or ready contact with the ciliary body. In aspects, the lens 100 is sized such that it is generally oversized relative to the ciliary structures. This can ensure contact between the force translation arms 115 and the ciliary structure during accommodation. In aspects, the lens is oversized by at least about 0.80 mm, 0.75 mm, 0.70 mm, 0.65 mm, 0.60 mm, 0.55 mm, or 0.05 mm to guarantee ciliary contact with the force translation arms 115. It should be appreciated that the lens need not be oversized and in some circumstances oversizing of the lens may be avoided. For example, accurate measurements of the ciliary diameter at the plane of the lens may be relied upon to ensure the fit of the lens is suitable and optimized for a particular patient.

The force translation arms 115 described herein can have a fixed length. The fixed length force translation arms 115 can have a size selected that is appropriate for each patient based on pre-operative measurements. Alternatively, the length of the force translation arms 115 can be adjustable. The adjustment of the force translation arms 115 length can be performed prior to, during, or any time after insertion in the eye. Along with the adjustment of the length of the force translation arms 115, the position of the force translation arms 115 relative to the one or more ciliary structures can vary. In aspects, the force translation arms 115 can extend generally parallel to the plane of the lens 100 or can be angled relative to the plane of the lens 100.

Contraction of the ciliary muscle and inward/anterior movement of one or more of the ciliary structures towards the optical axis A of the lens 100 applies a force against the contact portions 135 of the force translation arms 115. The force translation arms 115 are rigid enough relative to the deformation membrane 140 to transfer the forces applied by one or more moving parts of the eye (e.g. one or more ciliary structures) to cause inward movement of the deformation membrane 140. In aspects, the force translation arms 115 can be a rigid polymer such as silicone, polyurethane, PMMA, PVDF, PDMS, polyamide, polyimide, polypropylene, polycarbonate, etc., or combinations thereof. In aspects, the force translation arms 115 can be an element reinforced with a rigid material. For example, the force translation arms 115 can have an inner, rigid element such as silicone elastomer, polyurethane, PMMA, PVDF, PDMS, polyamide, polyimide, polypropylene, polycarbonate, etc. that is covered by a softer material such as silicone elastomer, polyurethane, or flexible acrylic materials that are hydrophobic or hydrophilic. In silicone, polyurethane, PMMA, PVDF, PDMS, polyamide, polyimide, polypropylene, polycarbonate, the force translation arms 115 can include an inner, rigid element that extends between the outer contact portion 135 to the inner contact portion 137. In silicone, polyurethane, PMMA, PVDF, PDMS, polyamide, polyimide, polypropylene, polycarbonate, the inner, rigid element extends only along a partial length of the force translation arms 115 between the outer portion 135 and the inner portion 137. For example, the inner, rigid element need not extend clear to the outer contact portion 135 where the force translation arms 115 make contact with the ciliary structures to provide a softer and atraumatic surface so as not to damage the ciliary structures. The inner, rigid element also need not extend clear to the inner contact portion 137 such that upon inward movement of the shape deformation membrane 140 by the force translation arm 115, the inner, rigid element of the force translation arm 115 remains outside the lens body 105. Generally, the force translation arms 115 are formed of a material and/or sized in a manner that they maintain their shape when forces are applied to them by a ciliary structure and they do not collapse or deform upon transferring that force to move the shape deformation membrane 140. As described above, movement of the shape deformation membrane 140 causes a shape change in the fluid chamber 155, which changes the shape of the liquid optical material contained within the fluid chamber 155. When the liquid optical material presses against the inner surfaces of the lens body 105 it causes an outward bowing in the dynamic membrane 143 of the anterior optic 145. This outward bowing results in a more spherical or convex lens body 105 shape thereby increasing the power of the lens suitable for near vision focus.

The number of force translation arms 115 and shape deformation membrane 140 can vary. The lens 100 can include two force translation arms 115 positioned on opposing sides of the device lying adjacent to two shape deformation membrane 140, as shown in FIG. 4E. Alternatively, the lens 100 can include a single force translation arm 115 movable in a manner sufficient to change the shape of the dynamic membrane 143 of the anterior optic 145 to achieve a desired dioptric change. The lens 100 can also include more than two arms, such as three, four, or more force translation arms 115 distributed around the lens body 105. The force translation arms 115 can be distributed in a symmetric manner around the perimeter of the lens 100 or in an asymmetric manner. It should be appreciated that the number of force translation arms 115 need not match the number of shape deformation membranes 140. For example, the lens 100 can include a single shape deformation membrane 140 extending along an arc length of the equator region of the lens body 105 and more than one force translation arms 115 configured to make contact with or coupled to different regions of the single shape deformation membrane 140.

The lens 100 can also include a stabilization system 120. The stabilization system 120 can be configured to maintain alignment of the optics of the device and resist movement of the device once the device is implanted and undergoing shape changes. Unlike the force translation arms 115, the stabilization system 120 does not cause accommodation of the lens 100. And because the force translation arms 115 are independent from the stabilization system 120 and are not necessary to fix, center, stabilize, and/or hold the lens 100 in position within the eye, the lenses 100 described herein can incorporate a single, asymmetric force translation arm 115 sufficient to provide the dioptric change of the dynamic membrane.

The stabilization system 120 can be coupled to a static zone of the device 100, for example, bonded, coupled, or molded as part of the lens body 105 or to an exterior support, if present. The stabilization system 120 can be coupled to a posterior region of the device 100 such that it can provide stabilization and engagement with a portion of the capsular bag, such as with the anterior capsule.

The stabilization system 120 can vary. The stabilization system 120 includes one or more of a stabilization haptic, static haptic, ring-like element, a flange element or wing, or other stabilizing feature. The stabilization system 120 can include one or more wings 172 extending outward from a region of the lens, such as the posterior end (see, for example, FIG. 4C). An anterior surface of a ring-like structure 171 can be coupled to a peripheral connecting surface of the lens body 105 or static element 150 such that the wing 172 extends posterior to the lens body 105. It should be appreciated, however, that any of a variety of coupling arrangements between the stabilization system 120 and the lens body 105 are considered herein. The ring-like structure 171 and wing 172 can be coupled to or integral with other portions of the lens body 105. Generally, the coupling of the stabilization system 120 to the lens body 105 is such that the wing 172 is positioned in a posterior position relative to the lens body 105 and to the force translation arms 115 along the optical axis A of the lens 100. Additionally, the stabilization system 120 and its components such as the wing 172 are coupled to the lens body 105 in a manner that does not interfere with movement of the force translation arms 115 and the shape deformation membrane 140. For example, as shown in FIG. 4A, the stabilization system 120 can include a pair of wings 172 that extend outward from the periphery of the lens body 105 between the location of the force translation arms 115. The wing 172 can have an outer elevation, but because they are positioned 90 degrees relative to the force translation arms 115 can provide stability without interfering with accommodative movements of the arms 115. Forces applied to the wing 172 or the ring-like structure 171 do not get transferred by the stabilization system 120 to the lens 100 in a manner that causes deformation of the fluid chamber 155 or shape change in the dynamic membrane 143. The wing 172 can be positioned in a posterior position relative to the lens body 105 and to the force translation arm 115. An anterior surface of the wing 172 may also be on the same plane as the force translation arm 115. The more anterior the wing 172, the greater the wing 172 can push the lens body 105 in a posterior direction. In an implementation, the wing 172 can urge the lens body 105 in a posterior direction while remaining below a plane of the force translation arms 115. FIG. 4D illustrates the wing 172 having an outer region that projects anteriorly relative to an inner region 178 of the wing 172. The inner region 178 of the wing 172 can be below (or posterior to) the plane P1 of the lens body 105 as well as below (or posterior to) the planes P2, P3, P4, P5 of the force translation arms 115 such that the inner region 178 is posterior to both the lens body 105 and the force translation arms 115. The outer region of the wing 172 projecting anteriorly can remain below the plane P1 of the anterior surface 106 of the lens body and also below the plane P2, P3 of the anterior-facing surface 116 of the force translation arms 115. In some implementations, the outer region of the wing 172 projecting anteriorly can lie above, within, or below the plane P4 of the anterior-facing surface 117 of the force translation arms 115. The plane P5 of the projection 179 of the arm 115 can extend posteriorly relative to the outer elevation of the wing 172 as shown in FIG. 4D.

The wing 172 can extend out beyond the outer diameter of the ring-like structure 171 in at least two regions along the perimeter of the lens body 105. The at least two regions where the wing 172 extends out beyond the outer diameter D1 of the lens body 105 can be oriented relative to the lens body 105 such that the wing 172 provides stabilization support relative to the force translation arms 115. For example, if the lens 100 includes a pair of opposing force translation arms 115, the wing 172 can be arranged relative to the lens body 105 such that the wing 172 extends outward from the lens body 105 between the location of the opposing force translation arms 115 and define an outer diameter D3 that is greater than the outer diameter D1 defined by the lens body and smaller than the outer diameter D2 defined by the force translation arms 115 (see, for example, FIG. 4H). It should be appreciated that the wing 172 can have any of a variety shapes including oval, elliptical, cylindrical and freeform. The wing 172 can also be annular and the outer diameter D3 configured to extend outward beyond the outer diameter D1 of the lens body 105 along 360 degrees. Alternatively, the wing 172 can have more than two locations where it extends beyond the outer diameter of the lens body 105 such as three, four, five, or more locations. The wing 172 can provide 360 degree support and stabilization to the lens 100. The outer diameter D1 defined by the lens body can be sized to be received snugly within the opening of the capsulorhexis, for example, between about 5.0 mm and about 9.0 mm, preferably about 6.5 mm. The outer diameter D2 defined by the force translation arms 115 can be sized to extend outside the capsular bag so as to engage with and harness movements of the ciliary body, for example, between about 8.5 mm and about 13.5 mm, or between about 10.2 mm and about 11.1 mm. The outer diameter D3 defined by the wings 172 can be sized to be received inside the capsular bag so as to extend beyond the edges of the capsulorhexis, for example, between about 6.0 mm and about 10.0 mm, preferably about 7.5 mm. In an implementation, the first outer diameter D1 can be between about 6.5 mm, the second outer diameter D2 can be between about 10.2 mm and 11.1 mmm and the third outer diameter D3 can be about 7.5 mm.

As mentioned above, a pair of wings 172 can be positioned between or rotated 90 degrees relative to the location of the force translation arms 115. An outermost edge of the wings 172 can project anteriorly such that a channel or groove 174 is formed near an inner region 178 of the wing 172, (see FIG. 4F). When the lens 100 is positioned within the eye, the outer elevation of the wings 172 can engage with a posterior-facing internal surface of the capsular bag (i.e., the anterior segment of the capsular bag) to help urge the lens 100 in a posterior direction relative to the bag. Additionally, the edge of the capsulorhexis can be received and held within the groove 174. In aspects, the edge of the capsulorhexis can be captured between the groove 174 and the wing 172 and a posterior-facing edge of the lens body 105. The groove 174 can define an outer diameter D4 that is even narrower than the outer diameter D1 defined by the lens body 105 (see FIG. 4H). The presence of the groove 174 and smaller outer diameter D4 means the opening in the capsular bag can be minimized. The larger outer diameter D1 of the lens body 105 can remain anterior to the opening in the bag so that the capsulorhexis in the bag need only encircle the smaller outer diameter D4 defined by the groove 174. The outer diameter D3 defined by the wings 172 can be larger than the size of the opening in the bag so that the wings 172 are prevented by slipping anterior to the opening in the bag once the IOL is positioned.

As described elsewhere herein, the force translation arms 115 are configured to extend outside the capsular bag 22 forming a larger outer diameter D2 sized to engage with ciliary structures such that the physiological forces from ciliary muscle contraction can cause a change in optical power of the lens in a manner that is independent of the capsular mechanism or movement of the capsular bag 22. The wing 172 extending outward from a posterior end region of the lens body 105 can define an outer diameter D3 sized to remain inside the capsular bag 22 posterior to the capsulorhexis while the force translation arms 115 extending generally from the equator region or anterior end region of the lens body 105 defining a larger outer diameter D2 that is sized to extend outside the capsular bag 22 to engage with the inner diameter of the ciliary structures. The wing 172 can be arranged to engage the posterior-facing surface of the edge of the capsular bag 22 formed by the anterior capsulorhexis to improve the fixation of the lens 100 within the eye. The edge of the capsular bag 22 formed by the capsulorhexis can be received within the groove 174 formed between the posterior surface of the lens element 105 and an anterior surface of the wing 172. The groove 174 allows for the edge of the capsular bag 22 to fit snugly with the smaller outer diameter D4 and capture the edge by the outer diameter D1 of the lens body 105 that can project anterior to the opening in the bag 22. The relative diameters of the lens body 105 and the groove 174 can thus, aid in fixing the lens position snugly with the capsulorhexis.

The wing 172 can have interruptions providing for flexibility during handling as well as allow the surgeon to access portions of the lens 100 and capsular bag 22 posterior to the wing 172. This may be preferred in case the surgeon needs to clean the capsular bag, remove viscoelastic, adjust the position of the lens, or any other procedure in which the surgeon uses a tool to manipulate the environment posterior to the lens. In aspects, the interruptions can include one or more apertures extending through a region of the wing 172 (not shown). The interruptions can also include one or more indentations, or grooves or other feature near an outer perimeter of the wing 172. The interruptions can allow for easy insertion into the eye as well as allow for natural egress of fluid and/or withdrawal of viscoelastic from inside the capsular bag 22 using a cannula or other tool known in the art.

Again with respect to FIG. 4C, the annular stabilization structure 171 positioned on a posterior side of the lens 100 can include a central opening 173 and a pair of wings 172 projecting outward from the annular stabilization structure 171. In aspects, the lens 100 can incorporate two force translation arms 115 and two wings 172. The wings 172 can be rotated 90 degrees around the circumference of the lens 100 relative to the arms 115 so that they are positioned between the two force translation arms 115. This arrangement prevents the outer elevation of the wings 172 from interfering with the motion of the force translation arms 115. FIG. 4B shows a side view of the lens 100 illustrating a plane of the outer elevation of the wings 172 extending upward toward a plane of the force translation arm 115. An inner region 178 of the wings 172 can lie within a plane that lies posterior to a plane P4, P5 of the posterior-facing surface 117 of the arms 115 (see FIG. 4D). The wings 172 can curve anteriorly towards their outer perimeter. A plane of the outer elevation of the wings 172 can lie posterior to a plane P4, P5 of the posterior-facing surface 117 of the arms 115 or as shown in FIG. 4D can extend above (or anterior to) a plane P4, P5 of the posterior-facing surface 117 of the arms 115 and below (or posterior to) a plane P2, P3 of the anterior-facing surface 116 of the arms 115.

The stabilization structure 171 can be sized and shaped to engage with corresponding surfaces of the lens body 105, such as posterior-facing surfaces of the posterior element 150. It should be appreciated the stabilization structure 171 can be molded as an integral part of the lens body 105 and need not be a separate component. Thus, where surfaces of components are described as being engaged with or bonded to one another it should be appreciated that this can include being molded together as a unitary piece.

The geometry of the stabilization structure 171 relative to the lens body 105 can improve fixation of the lens 100 within the capsular bag by capturing the edges of the capsulorhexis. An inner region 178 of the wings 172 can be separated a distance from the posterior-facing edge of the lens body 105 forming a groove between the lens body 105 and the inner region 178 of the wings 172 (see FIG. 4B). The stabilization system 120 of the lenses described herein are configured to insert within the capsular bag of the eye while accommodating components of the lens (e.g., force translation arms 115 and dynamic membrane 143) can extend outside the capsular bag. When the wings 172 are implanted within the capsular bag so that the outer elevation of the wings 172 engage the anterior portion of the capsular bag, the edge of the capsulorhexis can be received and held within the groove 174. The geometry of the stabilization structure 171 relative to the lens body 105 can also allow for fluid flow through the lens 100. For example, the coupling between the stabilization structure 171 and the lens body 105 can be discontinuous such that fluid trapped posterior to the lens 100 is allowed to escape the capsular bag even when the outer elevation of the wings 172 engages with the posterior-facing surface of the anterior segment of the bag and the capsulorhexis fits snugly around the perimeter of the lens body 105 (outer diameter D1) and/or within the smaller outer diameter D4 defined by the groove 174. The lens body 105 near the groove 174 can additionally incorporate one or more apertures, slots, or cut-outs 177 extending through a sidewall of the lens body 105. In aspects, a first cut-out 177 a sidewall of the lens body 105 can be positioned over an inner region 178 of a first wing 172 and a second cut-out 177 in the sidewall of the lens body 105 can be positioned over an inner region 178 of a second wing 172 (see FIG. 4B). The cut-outs 177 create a fluid channel (e.g., for egress of fluids like viscoelastic within the capsular bag) from a posterior side of the lens 100 (e.g., positioned within the capsular bag), between the stabilization structure 171 and the posterior element 150, through the cut-outs 177, and out an anterior side of the lens 100 (e.g., positioned inside the anterior chamber) (see arrow A in FIG. 4F). Thus, the lens 100 is prevented from sealing completely with the capsular bag even where the bag fits snug with the capsulorhexis. The size of the cut-outs 177 can vary. In aspects, the width of the cut-outs 177 approaches the width of the inner region of the wings 172. The cut-outs 177 allow for unimpeded flow of fluid through the lens 100 without impacting stability of the lens 100 during accommodative movements. The wings 172 can additionally incorporate one or more interruptions or apertures as described above.

Any of the stabilization systems described herein can be arranged to be coaxial or coplanar with the force translation arms 115 or positioned along a different axis than the force translation arms 115 such that the stabilization system 120 is offset from the force translation arms 115 or angled relative to them as described above with respect to the haptics. Similarly, the stabilization systems 120 can be angled relative to the force translation arms 115 such that at least a portion of the stabilization system 120 angles away from a plane of the lens such that at least a portion of the stabilization system sits on a different plane than another portion of the stabilization system.

It should be appreciated that any of the stabilization systems described herein can be formed from silicone elastomer, polyurethane, PMMA, PVDF, PDMS, polyamide, polyimide, polypropylene, polycarbonate, or flexible acrylic materials that are hydrophobic or hydrophilic or any combination of those materials. The stabilization system may have a softer body that is reinforced with more rigid structures in order to provide its stabilizing function while maintaining flexibility for insertion and manipulation.

One or more portions of the stabilization system 120 described herein can incorporate biting elements to improve fixation within the eye. In aspects, the stabilization system 120 includes haptics and the biting elements can be positioned near their terminal ends to improve fixation of the haptic within the eye. The stabilization haptics can be any of a variety of haptic designs or combination of haptic designs including, but not limited to open-loop, closed-loop, plate-style, plate loop, monoblock-plate style, j-loop, c-loop, modified J-loop, multi-piece, single-piece, angulated, planar, offset, etc. Haptics considered herein can include the Rayner designed haptics (Rayner Intraocular Lenses Ltd, East Sussex, UK), NuLens designed haptics (NuLens Ltd., Israel), Staar lens designs (Staar Surgical, Monrovia, CA), and others. In aspects, the stabilization system 120 whether including one or more haptics or a 360 degree wing can be formed of a biocompatible polymer such as silicone, polyurethane, PMMA, PVDF, PDMS, polyamide, polyimide, polypropylene, polycarbonate, PEEK, etc. or a combination of such materials. The stabilization system 120 can be formed of a material or configured to be foldable. In aspects, the stabilization system 120 is formed of a shape memory material.

The lenses described herein have improved mechanical stability, internally and/or externally, that results in a more efficient shape change. The shape change is more efficient in that it occurs only where desired (i.e. at the shape deformation membrane 140 and the dynamic membrane 143) without causing distortion or bulging elsewhere in the device that would take away from the desired shape change. The efficiency in shape change is due, in part, to the mechanical isolation of the moving parts due to, for example, the one or more supports providing enough rigidity to the lens 100 to mechanically isolate the moving parts to effectively and efficiently implement the shape change without inadvertent bulging or distortion in other parts of the device. The inner-facing region of the lenses 100 described herein can have reduced angles, rounded edges, and fewer dead zones improving the efficiency of the shape change achieved. These aspects together with the controlled continuous thickness gradient of the dynamic membrane between the periphery to the center provide the desired, predictable optical surface deflection for near vision.

The various components and features of the lenses described herein can be incorporated in any of a variety of combinations. As such, description of a particular feature shown with respect to a particular drawing is not intended to be limiting in that the feature can be incorporated into another implementation of a lens described herein. For example, the lenses described herein can include a stabilization system that incorporates one or more features of the stabilization systems described herein. Further, the lens having the stabilization system features can be combined with any of a variety of features described with respect to the force translation arm 115 or the shape deformation membrane 140, for example.

Suitable materials or combinations of materials for the preparation of the various solid optical components of the devices disclosed herein are provided throughout. It should be appreciated that other suitable materials are considered. U.S. Patent Publication Nos. 2009/0234449, 2009/0292355 and 2012/0253459, which are each incorporated by reference herein in their entirety, provide further examples of other materials suitable for forming certain components for the devices described herein. One or more solid optical components of the lens body 105 can be integral with one another in that they are formed of the same material. For example, the internal supports 110e can be thickened regions of the static anterior optical portion 144 of the anterior optic 145. Similarly, the shape deformation membrane 140 can be integral with one another having certain physical properties, such as a thickness or flexibility, to provide a desired function. Alternatively, one or more of the solid optical components of the lens body 105 can be coupled together by techniques known in the art. As such, the one or more solid optical components of the lens body 105 can be formed of the same materials or different materials. One or more of the supports 110, static anterior optical portion 144, dynamic membrane 145, and shape deformation membrane 140 can be formed of an optically clear, low modulus elastomer such as silicone, urethane, flexible acrylic, or flexible inelastic film such as polyethylene, as well as halogenated elastomers such as fluorosilicone elastomers. In aspects, the liquid optical material contained within the fluid chamber 155 can be a fluorosilicone oil and the solid optical components forming the fluid chamber 155 (e.g. inner-facing surfaces of the shape deformation membrane 140, the static element 150, the supports 110, the static anterior optical portion 144 and the dynamic membrane 143 of the anterior optic 145) are formed of a silicone elastomer. In aspects, the liquid optical material contained within the fluid chamber 155 is a silicone oil and the solid optical components forming the fluid chamber 155 are formed of a fluorosilicone elastomer. In aspects, the liquid optical material contained within the fluid chamber 155 is an aromatic or phenyl-substituted oil such as phenylsilicone oil and the solid optical components forming the fluid chamber 155 are formed of a halogenated silicone elastomer such as fluorosilicone elastomer. The combinations of materials are chosen to optimize stability of the lens, prevent swelling and maintaining optimum refractive index.

In aspects, the force translation arms 115 can be a rigid polymer formed of silicone, polyurethane, PMMA, PVDF, PDMS, polyamide, polyimide, polypropylene, polycarbonate, etc., or combinations thereof. In some implementations, the force translation arms 115 can be an element reinforced with PMMA. In aspects, the lens is formed of all silicone materials including the posterior static element 150 and the force translation arms 115. The stabilization system 120 can be formed of a more rigid silicone or can be formed of or incorporate polyimide. For example, the stabilization haptics and the wing 172 can be polyimide.

The lenses described herein can provide focusing power across the full accommodative range from distance to near by mechanically and functionally interacting with eye tissues typically used by a natural lens such as the ciliary body, ciliary processes, and the zonules, to effect accommodation and disaccommodation. The devices described herein can include an accommodative mechanism including one or more force translation arms configured to be positioned in the eye such that they harness movements of one or more ciliary structures and translate the movements into functional forces to drive shape change of the lens body for accommodation and disaccommodation in a manner independent of capsular bag movements. The lenses described herein can achieve an optical power change in the range of 1 diopter (1D) to 3D up to about 5D or 6D. The forces generated by these tissues are functionally translated to the devices described herein causing a power change to more effectively accommodate. The lenses described herein can further include a stabilization system separate from the accommodative mechanism that is configured to be positioned, for example, within the capsular bag. The devices described herein obviate known issues that tend to occur due to capsular fibrosis described above. It should be appreciated that the devices described herein can be configured to harness movements of one or combinations of ciliary structures including, but not limited to, the ciliary muscle, the ciliary body, ciliary processes, and zonules. For the sake of brevity, the term "ciliary structure" may be used herein to refer to any of the one or more ciliary structures for which movements can be harnessed by the force translation arms to effect accommodation of the lens body.

The devices described herein can be implanted in the eye to replace a diseased, natural lens. The devices can be implanted as a supplement of a natural lens (phakic patient) or an intraocular lens previously implanted within a patient's capsular bag (pseudophakic patient). The lenses described herein can be used in combination with intraocular lenses described in US 2009/0234449, US 2009/0292355, US 2012/0253459, WO 2015/148673, and WO 2018/081595, which are each incorporated by reference herein in their entirety. As such, the lenses described herein can be used independently or as so-called "piggyback" lenses. Piggyback lenses can be used to correct residual refractive errors in phakic or pseudophakic eyes. The primary lens used to replace the natural lens is generally thicker and usually has a power that can be in the range of ±10D to ±25D. The thicker, larger power lenses generally do not accommodate. In contrast, the supplemental lens need not provide significant optical power to the system. The supplemental lens can be relatively thin compared to the primary lens and can undergo more accommodation. Shape change and movement of the thinner lens is generally more easily accomplished relative to a thick primary lens. The lenses described herein can be used independently and need not be used in combination as piggyback lenses with the natural lens or an implanted lens. One or more components of the lenses described herein can be configured to be positioned in the sulcus 16, against the ciliary processes, within the capsular bag 22 or a combination thereof.

The devices and systems described herein can incorporate any of a variety of features. Elements or features of one implementation of a device and system described herein can be incorporated alternatively or in combination with elements or features of another implementation of a device and system described herein as well as the various implants and features described in US 2009/0234449, US 2009/0292355, US 2012/0253459, WO 2015/148673, and WO 2018/081595, which are each incorporated by reference herein in their entireties. For the sake of brevity, explicit descriptions of each of those combinations may be omitted although the various combinations are to be considered herein. The various devices can be implanted, positioned and adjusted etc. according to a variety of different methods and using a variety of different devices and systems. The various devices can be adjusted before, during as well as any time after implantation. Provided are some representative descriptions of how the various devices may be implanted and positioned, however, for the sake of brevity explicit descriptions of each method with respect to each implant or system may be omitted.

In aspects, description is made with reference to the figures. However, certain aspects may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detain in order to not unnecessarily obscure the description. Reference throughout this specification to "one embodiment," "an embodiment," "an aspect," "one aspect," "one implementation," "an implementation," or the like, means that a particular feature, structure, configuration, or characteristic described is included in at least one embodiment, aspect, or implementation. Thus, the appearance of the phrase "one embodiment," "an embodiment," "one aspect," "an aspect," "one implementation," "an implementation," or the like, in various placed throughout this specification are not necessarily referring to the same embodiment, aspect, or implementation. Furthermore, the particular features, structures, configurations, or characteristics may be combined in any suitable manner in one or more implementations.

The use of relative terms throughout the description may denote a relative position or direction or orientation and is not intended to be limiting. For example, "distal" may indicate a first direction away from a reference point. Similarly, "proximal" may indicate a location in a second direction opposite to the first direction. Use of the terms "front," "side," and "back" as well as "anterior," "posterior," "caudal," "cephalad" and the like or used to establish relative frames of reference, and are not intended to limit the use or orientation of any of the devices described herein in the various implementations.

The word "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples, embodiments, aspects, and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. An accommodating intraocular lens comprising:
an anterior optic positionable within an optic zone of an eye upon implantation in the eye, the anterior optic comprising:
a central, dynamic zone configured to undergo a shape change for accommodation comprising a dynamic membrane having a differential thickness gradient between a posterior surface and an anterior surface of the dynamic membrane, the posterior surface being substantially aspheric, and wherein the dynamic membrane has a first thickness between the posterior surface and the anterior surface at a center of the dynamic membrane and a second thickness between the posterior surface and the anterior surface at a periphery of the dynamic membrane, and wherein the first thickness is greater than the second thickness;
and a peripheral static zone comprising a static anterior optical portion configured to resist any shape change;
a posterior optic comprising an anterior surface positioned posterior to the anterior optic, the posterior optic being static and resistant to shape change and movement;
and a non-compressible optical fluid contained within a fluid chamber defined, in part, by the posterior surface of the dynamic membrane and the anterior surface of the posterior optic, wherein compression of the fluid chamber at a first region causes the shape change of the central, dynamic zone for accommodation, and wherein the differential thickness gradient of the dynamic membrane together with the peripheral static zone and the substantially aspheric posterior surface causes an external shape of the dynamic membrane when the anterior optic is in an accommodated state to have a single radius of curvature.

2. The accommodating intraocular lens of claim 1, wherein the anterior surface of the dynamic membrane is convex and the posterior surface of the dynamic membrane is convex.

3. The accommodating intraocular lens of claim 2, wherein both the anterior surface and the posterior surface control the differential thickness gradient of the dynamic membrane and the gradient changes between the periphery and the center of the dynamic membrane.

4. The accommodating intraocular lens of claim 1, wherein the anterior surface of the dynamic membrane is convex and the posterior surface of the dynamic membrane is concave.

5. The accommodating intraocular lens of claim 4, wherein both the anterior surface and the posterior surface control the differential thickness gradient of the dynamic membrane and the gradient changes gradually between the periphery and the center of the dynamic membrane.

6. The accommodating intraocular lens of claim 1, wherein the anterior surface of the dynamic membrane is convex and the posterior surface of the dynamic membrane is convex at the periphery of the dynamic membrane and plano near the center of the dynamic membrane.

7. The accommodating intraocular lens of claim 6, wherein both the anterior surface and the posterior surface control the differential thickness gradient of the dynamic membrane near the periphery and only the anterior surface controls the differential thickness gradient of the dynamic membrane at the center, wherein the gradient changes non-linearly between the periphery and the center of the dynamic membrane.

8. The accommodating intraocular lens of claim 6, wherein the anterior surface of the dynamic membrane has a convex curvature that follows a single radius or aspheric equation and wherein the posterior surface of the dynamic membrane near the periphery has a convex curvature that follows a single radius or aspheric equation.

9. The accommodating intraocular lens of claim 1, wherein the anterior surface of the dynamic membrane after accommodation is spherical, and wherein the optical fluid has a refractive index that is higher than or equal to a refractive index of the anterior optic.

10. The accommodating intraocular lens of claim 1, wherein, prior to the shape change when the anterior optic is in a disaccommodated state, both the anterior surface of the dynamic membrane and the posterior surface of the dynamic membrane are curved, and wherein a radius of curvature of the posterior surface is different from a radius of curvature of the anterior surface.

11. The accommodating intraocular lens of claim 1, wherein the optical fluid has a refractive index that is index-matched to the anterior optic.

12. The accommodating intraocular lens of claim 1, wherein the optical fluid has a refractive index that is higher than a refractive index of the anterior optic.

* * * * *